(12) United States Patent
Sgroi, Jr.

(10) Patent No.: US 11,076,858 B2
(45) Date of Patent: Aug. 3, 2021

(54) SINGLE USE ELECTRONICS FOR SURGICAL DEVICES

(71) Applicant: Covidien LP, Mansfield, MA (US)

(72) Inventor: Anthony Sgroi, Jr., Wallingford, CT (US)

(73) Assignee: COVIDIEN LP, Mansfield, MA (US)

( * ) Notice: Subject to any disclaimer, the term of this patent is extended or adjusted under 35 U.S.C. 154(b) by 142 days.

(21) Appl. No.: 16/451,191

(22) Filed: Jun. 25, 2019

(65) Prior Publication Data

US 2020/0054337 A1  Feb. 20, 2020

Related U.S. Application Data

(60) Provisional application No. 62/718,512, filed on Aug. 14, 2018.

(51) Int. Cl.
*A61B 17/115* (2006.01)
*A61B 17/072* (2006.01)
(Continued)

(52) U.S. Cl.
CPC ........ *A61B 17/1155* (2013.01); *A61B 17/072* (2013.01); *A61B 90/08* (2016.02);
(Continued)

(58) Field of Classification Search
CPC ......... A61B 90/08; A61B 34/00; A61B 34/71; B23P 11/00
See application file for complete search history.

(56) References Cited

U.S. PATENT DOCUMENTS 2,777,340 A   1/1957  Hettwer et al.
2,957,353 A   10/1960  Babacz
(Continued)

FOREIGN PATENT DOCUMENTS

CA   2451558 A1   1/2003
CN   1547454 A    11/2004
(Continued)

OTHER PUBLICATIONS

Extended European Search Report corresponding to International Application No. EP 14 18 4882.0 dated May 12, 2015.
(Continued)

*Primary Examiner* — Nathaniel C Chukwurah

(57) ABSTRACT

A handheld electromechanical surgical device includes a handle assembly, an adapter assembly, a reload, and an electrical assembly. The handle assembly includes a connecting portion having an electrical connector supported therein. The adapter assembly includes an adapter housing selectively connectable to the connecting portion of the handle assembly and an outer tube extending distally from the adapter housing. The reload includes a housing selectively connectable to the outer tube of the adapter assembly and a circuit board assembly disposed within the reload housing. The electrical assembly includes a flex cable having an elongate body positionable against an outer surface of the adapter assembly. A proximal end of the flex cable is positionable within a cavity defined in the adapter housing and configured to electrically connect with the electrical connector of the handle assembly. A distal end of the flex cable is coupled to the circuit board assembly of the reload.

10 Claims, 19 Drawing Sheets

(51) Int. Cl.
*A61B 90/00* (2016.01)
*A61B 17/00* (2006.01)
(52) U.S. Cl.
CPC ............... *A61B 2017/0046* (2013.01); *A61B 2017/00398* (2013.01); *A61B 2017/00725* (2013.01); *A61B 2017/00734* (2013.01); *A61B 2017/07214* (2013.01); *A61B 2090/0808* (2016.02); *A61B 2090/0811* (2016.02); *A61B 2090/0813* (2016.02)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |

(56) References Cited

U.S. PATENT DOCUMENTS

| | | |
|---|---|---|
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |

(56) References Cited

U.S. PATENT DOCUMENTS

| | | |
|---|---|---|
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0310134 A1 | 10/2016 | Contini et al. |

(56) References Cited

U.S. PATENT DOCUMENTS

| | | | | |
|---|---|---|---|---|
| 2017/0224347 | A1* | 8/2017 | Collins | A61B 17/00234 |
| 2018/0360460 | A1 | 12/2018 | Mozdzierz et al. | |

FOREIGN PATENT DOCUMENTS

| | | | |
|---|---|---|---|
| CN | 1957854 | A | 5/2007 |
| CN | 101495046 | A | 7/2009 |
| CN | 102247182 | A | 11/2011 |
| DE | 102008053842 | A1 | 5/2010 |
| EP | 0705571 | A1 | 4/1996 |
| EP | 1563793 | A1 | 8/2005 |
| EP | 1769754 | A1 | 4/2007 |
| EP | 2316345 | A1 | 5/2011 |
| EP | 2668910 | A2 | 12/2013 |
| ES | 2333509 | A1 | 2/2010 |
| JP | 2005125075 | A | 5/2005 |
| KR | 20120022521 | A | 3/2012 |
| WO | 2011108840 | A2 | 9/2011 |
| WO | 2012/040984 | A1 | 4/2012 |

OTHER PUBLICATIONS

Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.

* cited by examiner

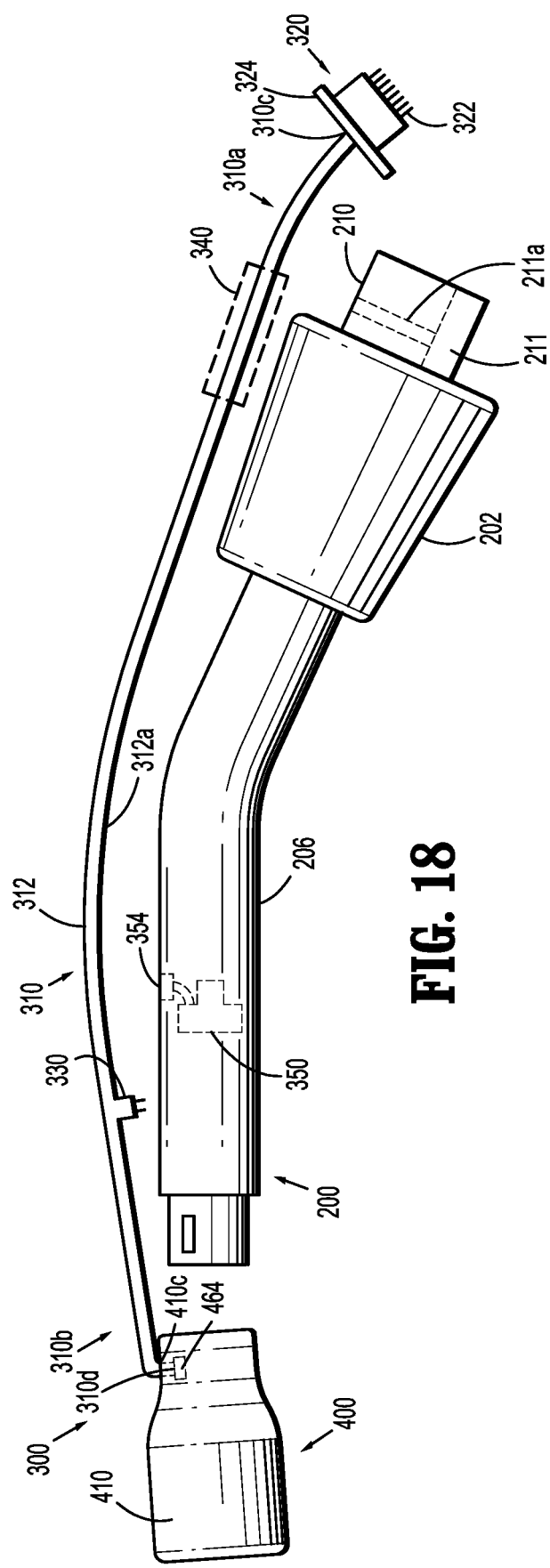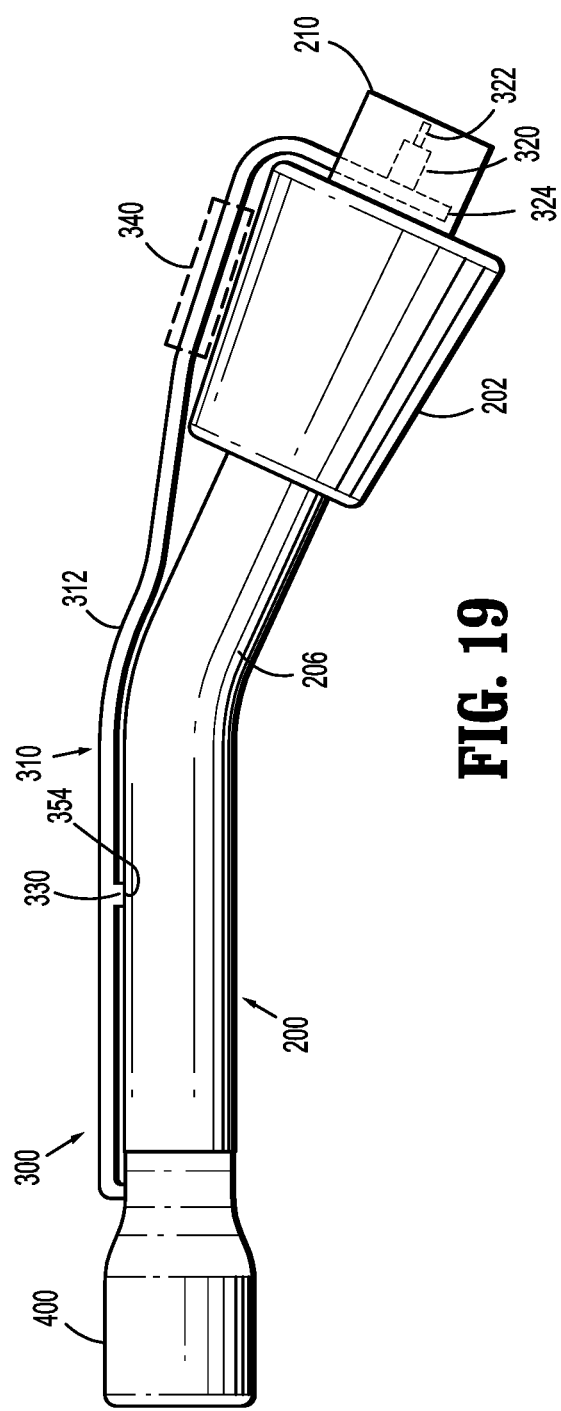

SINGLE USE ELECTRONICS FOR SURGICAL DEVICES

CROSS-REFERENCE TO RELATED APPLICATIONS

This application claims the benefit of and priority to U.S. Provisional Patent Application Ser. No. 62/718,512 filed Aug. 14, 2018, the entire disclosure of which is incorporated by reference herein.

BACKGROUND

1. Technical Field

The present disclosure relates to powered surgical devices. More specifically, the present disclosure relates to reusable handheld electromechanical surgical devices including low cost single use electronic components.

2. Background of Related Art

Powered surgical devices include electronic components, such as printed circuit boards, switches, sensors, etc., to enhance the control of functions of the surgical devices. The intelligence of such surgical devices result in a higher product cost compared to currently available disposable units. Accordingly, it would be beneficial if such intelligent devices are reusable.

For example, surgical devices in the form of surgical stapling apparatus are employed by surgeons to sequentially or simultaneously apply one or more rows of fasteners, e.g., staples or two-part fasteners, to body tissue for the purpose of joining segments of body tissue together and/or attaching a surgical implant to body tissue. Surgical stapling apparatus are used to perform various stapling functions in surgery, such as performing anastomosis of tubular body structures (e.g., the colon, the stomach, the small intestine, etc.) in an end to end, end to side, or side to side manner. Disposable surgical stapling apparatus are discarded after a single use while reusable surgical stapling apparatus may be used multiple times which may result in a lower cost per procedure over the life of the device.

Moreover, powered surgical stapling apparatus include electronic components to monitor and facilitate functions, such as clamping, stapling, and/or cutting forces of the device. For example, load reading sensors can be used to detect pre-set loads and cause the device to react to such a response. For instance, during clamping of thick tissue, the load will rise to a pre-determined limit where the device can slow clamping to maintain the clamping force as the tissue relaxes. This allows for clamping of thick tissue without damage to such tissue (e.g., serosa tears).

Reusable surgical devices must be cleaned and sterilized prior to subsequent uses. Cleaning and sterilization procedures, however, are aggressive in nature. Cleaning (e.g., washing and/or disinfecting) utilizes alkaline solutions (e.g., potassium hydroxide) having high pH values (e.g., a pH of 11). Autoclaving, a common method of sterilization, utilizes high pressure superheated steam (e.g., 30 PSI@160° C. for 20 minutes). Such environments are known to damage electronic components. For example, surgical devices may suffer from moisture ingress during cleaning and/or sterilizing procedures which, in turn, may corrode and/or degrade the electronic components.

It would be beneficial to have reusable powered surgical devices that utilize disposable or single-use electronic assemblies so that the electronic components are not subjected to the harsh environment of cleaning and sterilization processes.

SUMMARY

In accordance with aspects of the present disclosure, a handheld electromechanical surgical device includes a handle assembly, an adapter assembly, a reload, and an electrical assembly. The handle assembly includes a connecting portion having an electrical connector supported therein. The adapter assembly includes an adapter housing and an outer tube extending distally from the adapter housing. The adapter housing is selectively connectable to the connecting portion of the handle assembly. The reload includes a reload housing selectively connectable to the outer tube of the adapter assembly and a circuit board assembly disposed within the reload housing. The electrical assembly includes a flex cable having an elongate body positionable against an outer surface of the adapter assembly. The flex cable includes a proximal end positionable within a cavity defined in the adapter housing and configured to electrically connect with the electrical connector of the handle assembly, and a distal end coupled to the circuit board assembly of the reload.

The proximal end of the flex cable may include a pin connector assembly. The pin connector assembly may be configured to interface with the electrical connector of the handle assembly. In some aspects, the pin connector assembly includes electrical contact blades supported on a circuit board. The electrical contact blades are configured to contact the electrical connector of the handle assembly when the adapter assembly is connected to the handle assembly.

The distal end of the flex cable may be permanently secured to the circuit board assembly of the reload. A distal portion of the flex cable may extend through a port defined in the reload housing. The flex cable may include an adhesive disposed on a first side of the elongate body of the flex cable and positionable against the outer surface of the adapter assembly.

The outer tube of the adapter assembly may include an electrical connector secured therein. The electrical connector may be electrically coupled to a strain sensor supported within the outer tube. The flex cable may include a strain sensor electrical connector configured to mate with the electrical connector of the adapter assembly.

The flex cable may include a printed circuit board disposed or integrated thereon. In some aspects, the printed circuit board is positioned along a proximal portion of the flex cable aligned with the adapter housing of the adapter assembly. Wings may extend laterally from the printed circuit board of the flex cable. The wings may include an adhesive for securing the printed circuit board to the adapter assembly.

In accordance with aspects of the present disclosure, an end effector configured for selective connection with an adapter assembly includes a reload and an electrical assembly. The reload includes a reload housing and a circuit board assembly disposed within the reload housing. The electrical assembly includes a flex cable having an elongate body including a proximal end and a distal end. The proximal end is coupled to a pin connector assembly and the distal end is coupled to the circuit board assembly of the reload.

The pin connector assembly may include electrical contact blades supported on a circuit board. The distal end of the flex cable may be permanently secured to the circuit board assembly of the reload. A distal portion of the flex cable may extend through a port defined in the reload housing. The flex cable may include an adhesive disposed on a first side of the elongate body of the flex cable.

The flex cable may include a strain sensor electrical connector coupled thereto. The flex cable may include a printed circuit board disposed or integrated thereon. The printed circuit board may be positioned along a proximal portion of the flex cable. Wings may extend laterally from the printed circuit board. The wings may include an adhesive disposed thereon.

In accordance with further aspects of the present disclosure, a method of assembling a handheld electromechanical surgical device includes: positioning a pin connector assembly of an electrical assembly within a cavity defined in an adapter housing of an adapter assembly, the electrical assembly including a flex cable having an elongate body including a proximal end and a distal end, the proximal end coupled to the pin connector assembly and the distal end coupled to a circuit board assembly of a reload; extending the elongate body of the flex cable along an outer surface of the adapter assembly; securing the reload to an outer tube of the adapter assembly; and connecting a strain sensor electrical connector of the electrical assembly to an electrical connector secured within the outer tube of the adapter assembly, the electrical connector electrically coupled to a strain sensor supported within the adapter assembly.

BRIEF DESCRIPTION OF THE DRAWINGS

Embodiments of the present disclosure are described herein with reference to the accompanying drawings, wherein:

FIG. 18 is a side view of the adapter assembly and the end effector of FIG. 1, with the end effector separated from the anvil assembly;

FIG. 19 is a side view of the adapter assembly and the end effector of FIG. 18, with the end effector assembled with the anvil assembly;

DETAILED DESCRIPTION OF EMBODIMENTS

Figure 1:
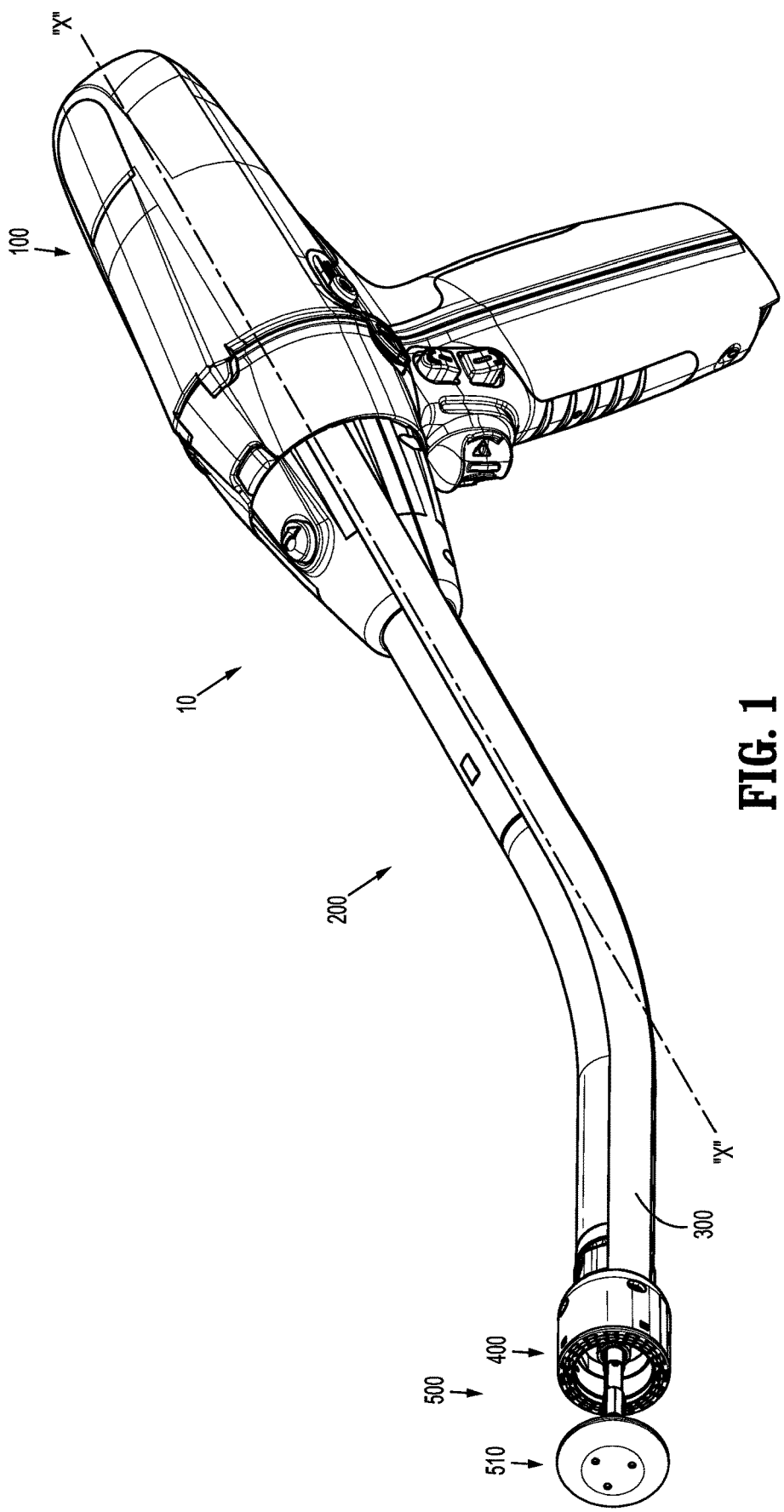
FIG. 1 is a perspective view of a handheld surgical device including a handle assembly, an adapter assembly, and an end effector in accordance with an embodiment of the present disclosure.

Embodiments of the present disclosure are now described in detail with reference to the drawings, in which like reference numerals designate identical or corresponding elements in each of the several views. As used herein the term "proximal" refers to a portion of a surgical device, or component thereof, closer to the user, and the term "distal" refers to a portion of the surgical device, or component thereof, farther from the user.

Turning now to FIG. 1, a surgical device 10, in accordance with an embodiment of the present disclosure, is in the form of a powered handheld electromechanical instrument. The surgical device includes a handle assembly 100, an adapter assembly 200, and an end effector 500 including an electrical assembly 300, a reload 400, and an anvil assembly 510. The handle assembly 100 is configured for selective connection with the adapter assembly 200 and, in turn, the adapter assembly 200 is configured for selective connection with the end effector 500.

The handle assembly 100, the adapter assembly 200, and the end effector 500 will only further be described to the extent necessary to disclose aspects of the present disclosure. For a detailed description of the structure and function of exemplary handle assemblies, adapter assemblies, and end effectors, reference may be made to commonly owned U.S. Patent Appl. Pub. No. 2016/0310134 and U.S. patent application Ser. No. 15/972,606, the entire content of each of which is incorporated herein by reference.

Figure 2:
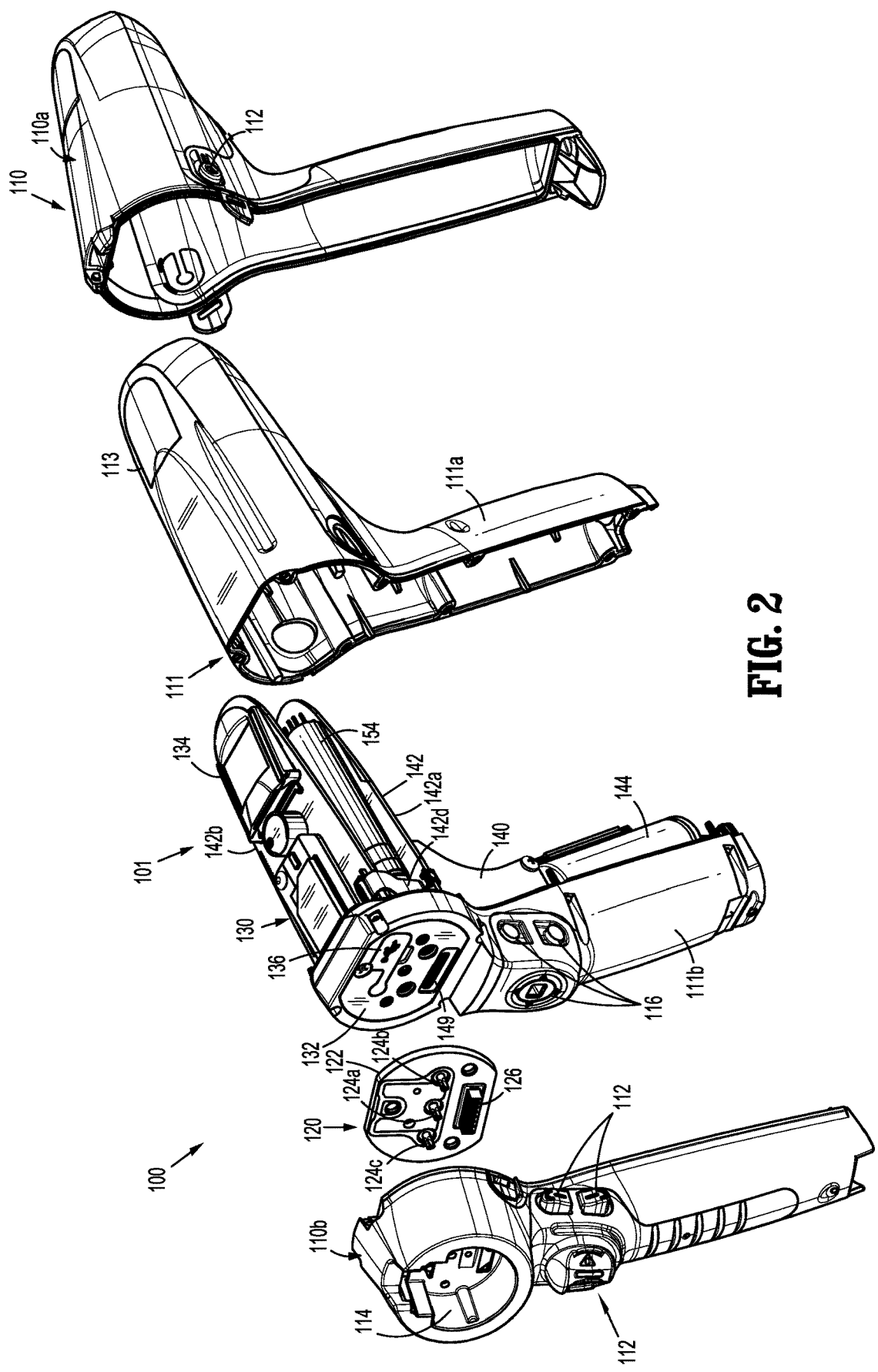
FIG. 2 is a perspective view, with parts separated, of the handle assembly of FIG. 1.

With reference now to FIG. 2, the handle assembly 100 includes a power handle 101 and an outer or shell housing 110 configured to selectively receive and encase the power handle 101. The shell housing 110 includes a proximal half-section 110a and a distal half-section 110b that are couplable together. The shell housing 110 includes a plurality of actuators 112 (e.g., finger-actuated control buttons, knobs, toggles, slides, interfaces, and the like) for activating various functions of the surgical device 10 (FIG. 1) upon application of a respective force thereto.

The distal half-section 110b of the shell housing 110 defines a connecting portion 114 (e.g., a recess) configured to accept or receive a corresponding drive coupling assembly 210 (FIG. 5) of the adapter assembly 200. A sterile barrier plate assembly 120 is selectively supported in the distal half-section 110*b* of the shell housing 110 behind the connection portion 114. The plate assembly 120 includes a plate 122 rotatably supporting three coupling shafts 124*a*, 124*b*, 124*c*, and having an electrical connector 126 supported thereon. The electrical connector 126 includes a chip and defines a plurality of contact paths each including an electrical conduit for extending an electrical connection across the plate 122. When the plate assembly 120 is disposed within the shell housing 110, distal ends of the coupling shafts 124*a*, 124*b*, 124*c* and the electrical connector 126 are disposed or situated within the connecting portion 114 of the shell housing 110 to electrically and/or mechanically engage respective corresponding features of the adapter assembly 200, as will be described in greater detail below.

The power handle 101 has an inner handle housing 111 including a proximal half section 111*a* and a distal half section 111*b* that are coupled together to house a power-pack core assembly 130 therein. The power-pack core assembly 130 is configured to control the various operations of the handle assembly 100 and thus, the surgical device 10.

The distal half section 111*b* of the inner handle housing 111 is configured and adapted to support a control plate 132 of the power-pack core assembly 130 such that the control plate 132 abuts the plate assembly 120 of the shell housing 110 when the power handle 101 is disposed within the shell housing 110. The distal half section 111*b* of the inner handle housing 111 also supports a plurality of actuator interfaces 116 that are in operative registration with the respective actuators 112 of the shell housing 110.

Figure 3:
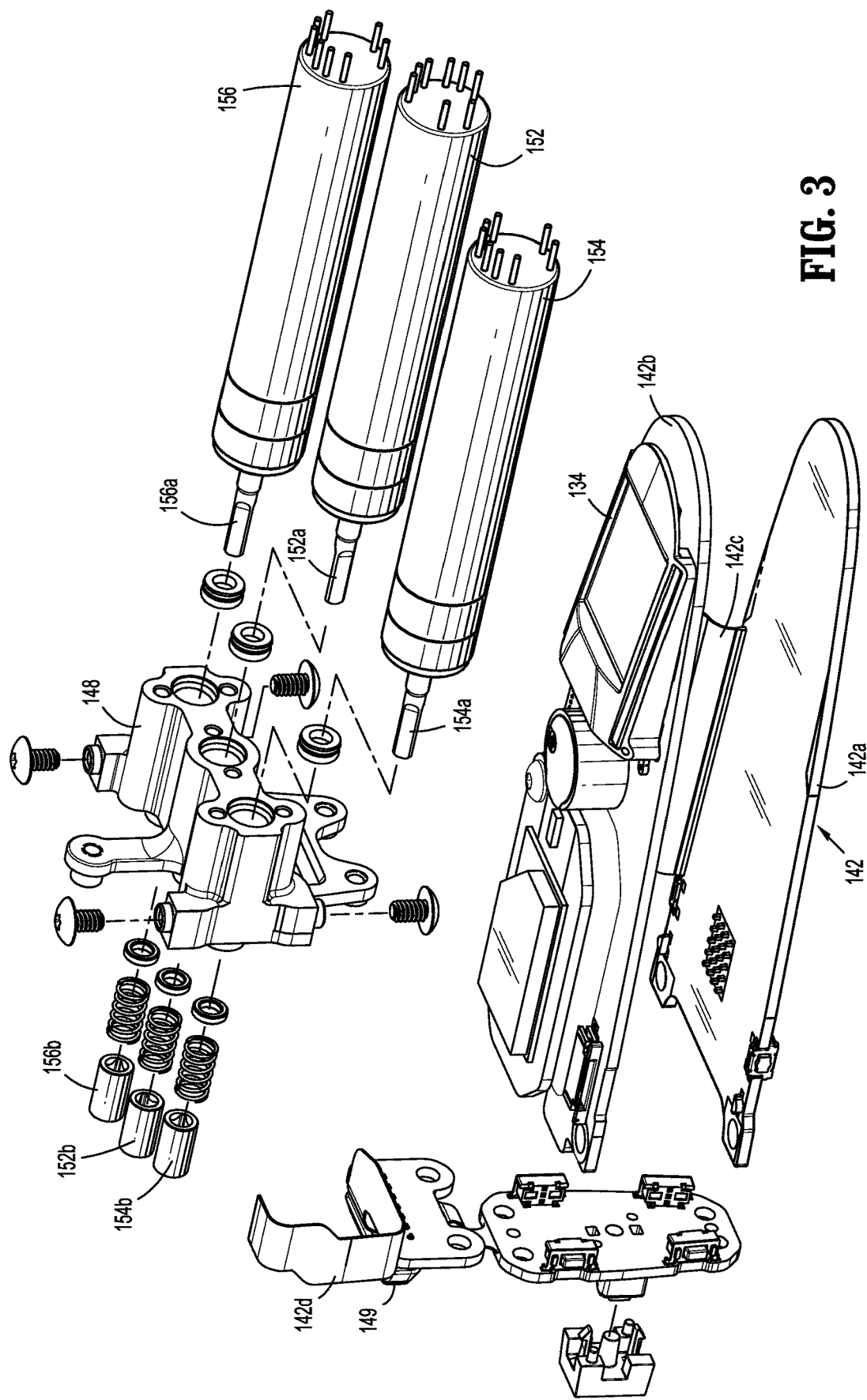
FIG. 3 is a perspective view, with parts separated, of a motor assembly and a control assembly of a power handle of the handle assembly of FIG. 2.

As shown in FIGS. 2 and 3, the power-pack core assembly 130 includes a battery circuit 140, a controller circuit board 142, and a rechargeable battery 144 configured to supply power to any of the electrical components of the handle assembly 100. The controller circuit board 142 includes a motor controller circuit board 142*a*, a main controller circuit board 142*b*, and a first ribbon cable 142*c* interconnecting the motor controller circuit board 142*a* and the main controller circuit board 142*b*. A display screen 134 is supported on the main controller circuit board 142*b* and visible through a clear or transparent window 113 provided in the proximal half-section 111*a* of the inner handle housing 111. A USB connector 136 (or other data connector) is also supported on the main controller circuit board 142*b* and is accessible through the control plate 132 of the power-pack core assembly 130.

The power-pack core assembly 130 further includes a first motor 152, a second motor 154, and a third motor 156 disposed between the motor controller circuit board 142*a* and the main controller circuit board 142*b*. Each of the first, second, and third motors 152, 154, 156 is electrically connected to the controller circuit board 142 and the battery 144, and controlled by a respective motor controller disposed on the motor controller circuit board 142*a* which, in turn, is coupled to a respective main controller disposed on the main controller circuit board 142*b*.

Each of the first, second, and third motors 152, 154, 156 is supported on a motor bracket 148 such that respective motor shaft 152*a*, 154*a*, 156*a* extending from the first, second, and third motors 152, 154, 156 are rotatably disposed within respective apertures of the motor bracket 148. The motor bracket 148 rotatably supports three rotatable drive connector sleeves 152*b*, 154*b*, 156*b* that are keyed to the respective motor shafts 152*a*, 154*a*, 156*a* of the first, second, and third motors 152, 154, 156. The drive connector sleeves 152*b*, 154*b*, 156*b* non-rotatably receive proximal ends of the respective coupling shafts 124*a*, 124*b*, 124*c* of the plate assembly 120 of the shell housing 110, when the power handle 101 is disposed within the shell housing 10, and are each spring biased away from the respective motors 152, 154, 156.

The motor bracket 148 also supports an electrical receptacle 149. The electrical receptacle 149 is in electrical connection with the main controller circuit board 142*b* by a second ribbon cable 142*d*. The electrical receptacle 149 defines a plurality of electrical slots for receiving respective electrical contacts or blades extending from the pass-through connector 126 of the plate assembly 120 of the shell housing 110.

Rotation of the motor shafts 152*a*, 154*a*, 156*a* by the respective first, second, and third motors 152, 154, 156 function to drive shafts and/or gear components of the adapter assembly 200 in order to perform the various operations of the handle assembly 100, as will be described in greater detail below.

In use, when the adapter assembly 200 is mated to the handle assembly 100, each of the coupling shafts 124*a*, 124*b*, 124*c* of the handle assembly 100 couples with a corresponding rotatable connector sleeve 218, 222, 220 (FIG. 6) of the adapter assembly 200. In this regard, the interface between corresponding coupling shafts 124*a*, 124*b*, 124*c* and connector sleeves 218, 222, 220 are keyed such that rotation of each of the coupling shafts 124*a*, 124*b*, 124*c* of the handle assembly 100 causes a corresponding rotation of the corresponding connector sleeve 218, 222, 220 of the adapter assembly 200.

The coupling shafts 124*a*, 124*b*, 124*c* of handle assembly 100 are configured to be independently rotated by the respective motor 152, 154, 156 such that rotational force(s) are selectively transferred from the motors 152, 154, 156 of the handle assembly 100 to the adapter assembly 200. The selective rotation of the coupling shaft(s) 124*a*, 124*b*, 124*c* of the handle assembly 100 allows the handle assembly 100 to selectively actuate different functions of the reload 400.

Figure 4:
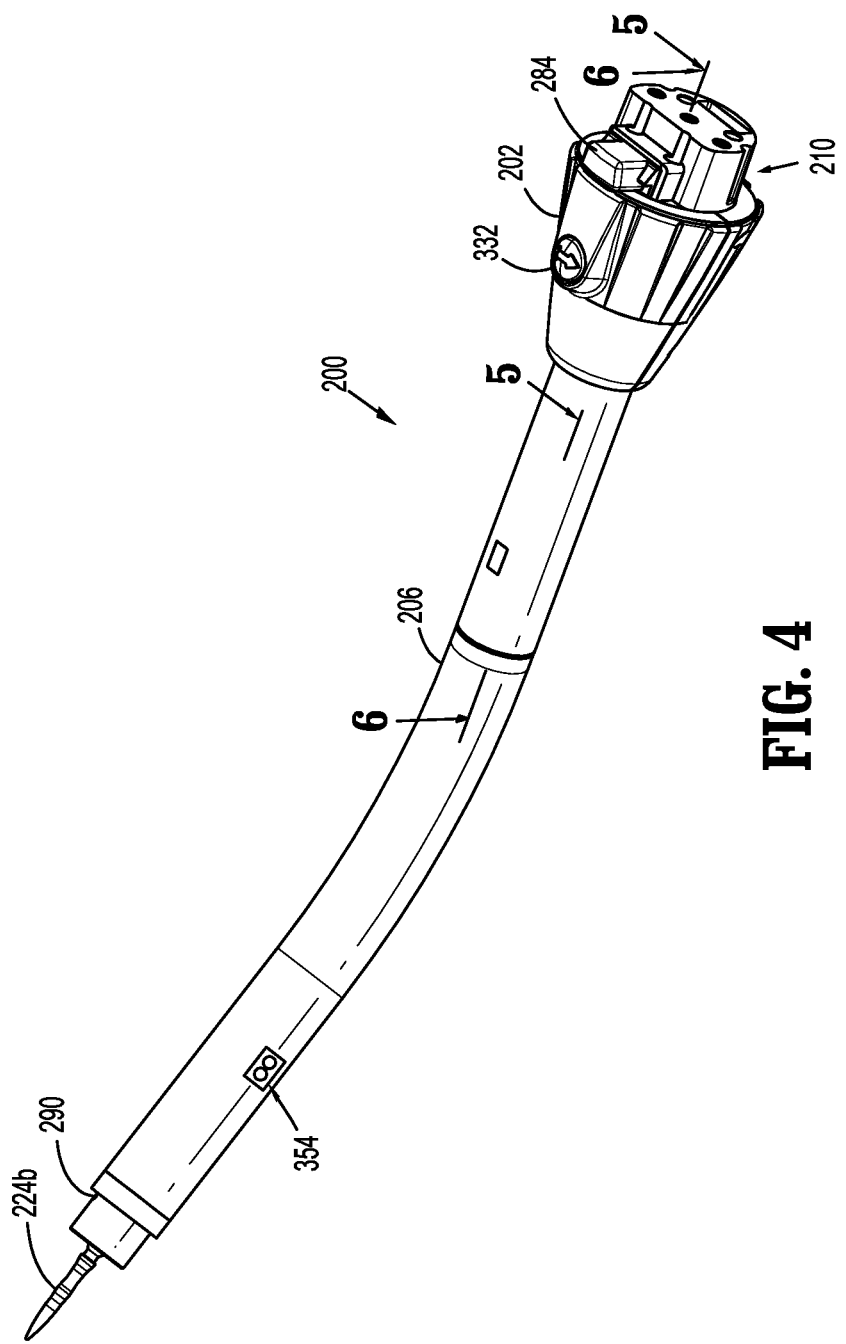
FIG. 4 is a perspective view of the adapter assembly of FIG. 1.

Turning now to FIG. 4, the adapter assembly 200 is configured to convert a rotation of the coupling shaft(s) 124*a*, 124*b*, 124*c* (FIG. 2) of the handle assembly 100 into axial translation useful for effecting various functions of the surgical device 10 (FIG. 1). The adapter assembly 200 includes an adapter or knob housing 202 and an outer tube 206 extending from a distal end of the knob housing 202. The knob housing 202 and the outer tube 206 are configured and dimensioned to house and support the components of the adapter assembly 200. The knob housing 202 includes a drive coupling assembly 210 which is configured and adapted to connect to the connecting portion 114 (FIG. 2) of the shell housing 110 of the handle assembly 100. The outer tube 206 includes a connector sleeve 290 fixedly supported at a distal end thereof. The connector sleeve 290 is configured to selectively secure the reload 400 (FIG. 1) to the adapter assembly 200.

Figure 5:
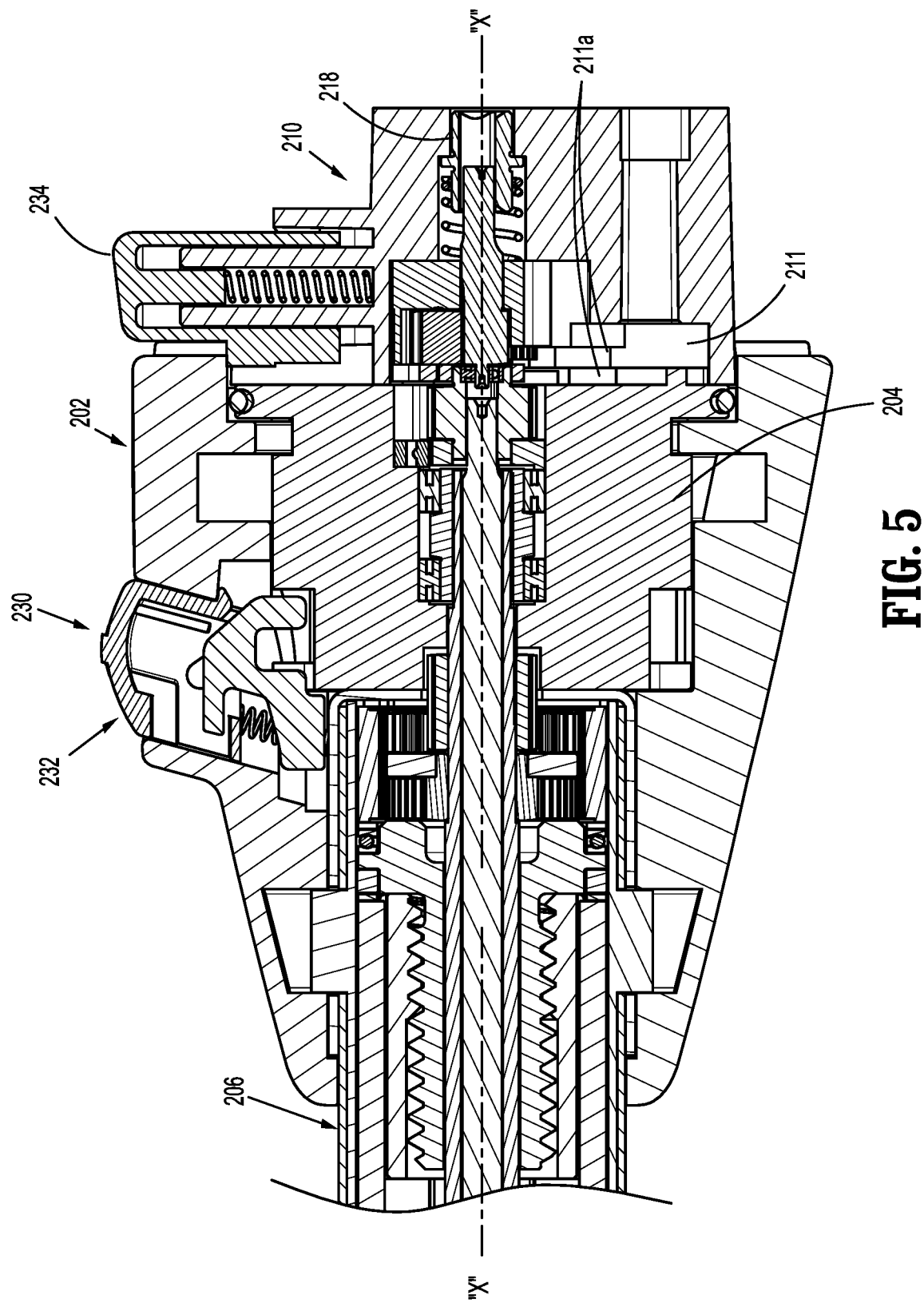
FIG. 5 is a cross-sectional view of the adapter assembly of FIG. 4, as taken through section line 5-5 of FIG. 4.

As shown in FIGS. 4 and 5, the adapter assembly 200 includes a rotation assembly 230 configured to enable rotation of the adapter assembly 200 relative to the handle assembly 100. Specifically, the knob housing 202 and the outer tube 206 of the adapter assembly 200 are rotatable relative to the drive coupling assembly 210 of the adapter assembly 200. The rotation assembly 230 includes a lock button 232 operably supported on the knob housing 202 and configured for actuating the rotation assembly 230. When rotation assembly 230 is in an unlocked configuration, the knob housing 202 and the outer tube 206 are rotatable along a longitudinal axis "X" of the adapter assembly 200 relative to the drive coupling assembly 210. When rotation assembly 230 is in a locked configuration, the knob housing 202 and the outer tube 206 are rotationally secured relative to the drive coupling assembly 210.

The adapter assembly 200 further includes an attachment/detachment button 234 supported on the drive coupling assembly 210 of the adapter assembly 200. In use, when the adapter assembly 200 is connected to the shell housing 110 of the handle assembly 100, the attachment/detachment button 234 secures and retains the adapter assembly 200 and the handle assembly 100 with one another. When the attachment/detachment button 234 is depressed or actuated, the adapter assembly 200 and the handle assembly 100 may be disconnected from each other.

The adapter assembly 200 further includes a cavity 211 defined within the drive coupling assembly 210 that is configured to receive a pin connector assembly 320 (FIG. 18) of an electrical assembly 300 configured for establishing an electrical connection with and between the handle assembly 100, the adapter assembly 200, and the reload 400, as described in further detail below. The cavity 211 may include guiding ribs 211 configured to receive a printed circuit board 324 of the pin connector assembly 320.

Figure 6:
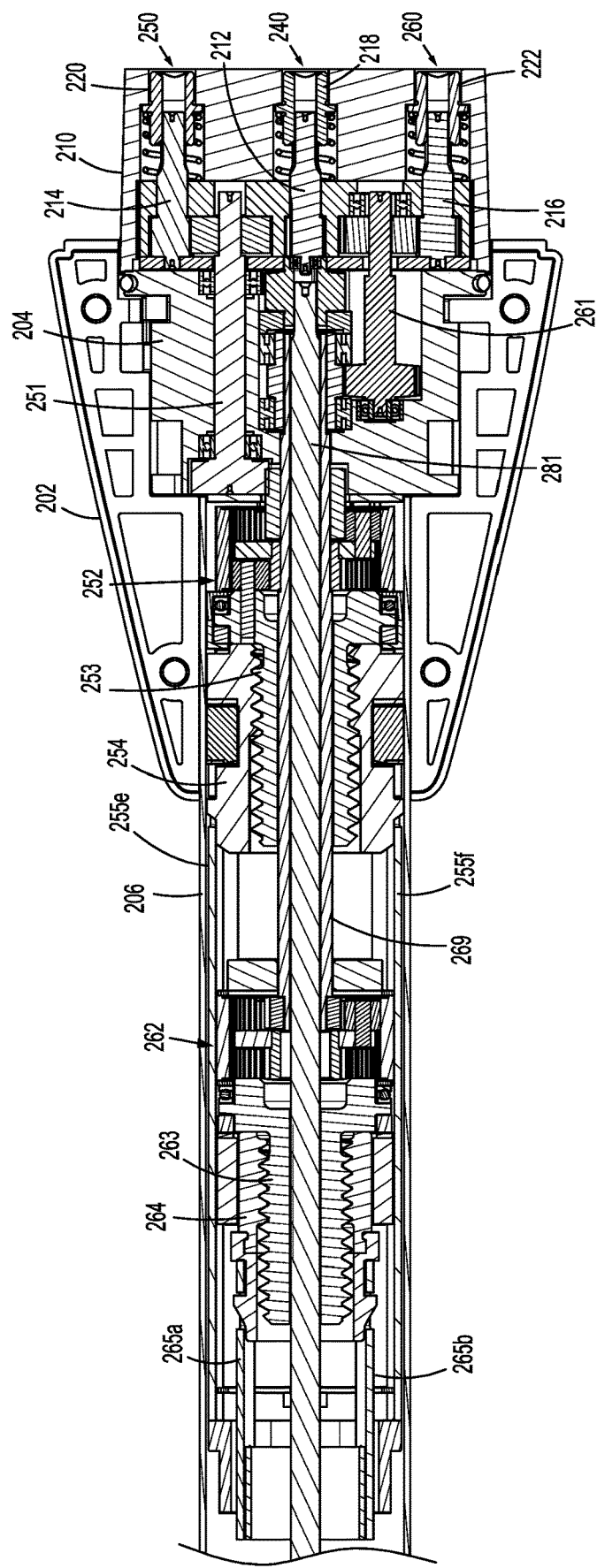
FIG. 6 is a cross-sectional view of the adapter assembly of FIG. 4, as taken through section line 6-6 of FIG. 4.

As illustrated in FIG. 6, the drive coupling assembly 210 of the adapter assembly 200 rotatably supports first, second, and third connector sleeves 218, 220 and 222 therein, and an inner housing member 204 disposed within the knob housing 202 rotatably supports first, second, and third rotatable proximal drive shafts 212, 214, 216 therein. Each of the first, second, and third connector sleeves 218, 220, 222 is configured to mate with a respective coupling shaft 124a, 124c, 124b (FIG. 2) of the handle assembly 100. Each of the first, second, and third connector sleeves 218, 220, 222 is further configured to mate with a proximal end of the respective first, second, and third proximal drive shafts 212, 214, 216 of the adapter assembly 200 such that each of the first, second, and third proximal drive shafts 212, 214, 216 functions as a rotation receiving member to receive rotational forces from the respective coupling shafts 124a, 124c, 124b of the handle assembly 100.

The adapter assembly 200 includes first, second and third force/rotation transmitting/converting assemblies 240, 250, 260 disposed within the inner housing member 204 and the outer tube 206. Each of the force/rotation transmitting/converting assemblies 240, 250, 260 is configured and adapted to transmit or convert a rotation of the respective coupling shaft 124a, 124c, 124b of the handle assembly 100 into axial translation to effectuate operation of the reload 400 (FIG. 1), as will be described in greater detail below.

Figure 7:
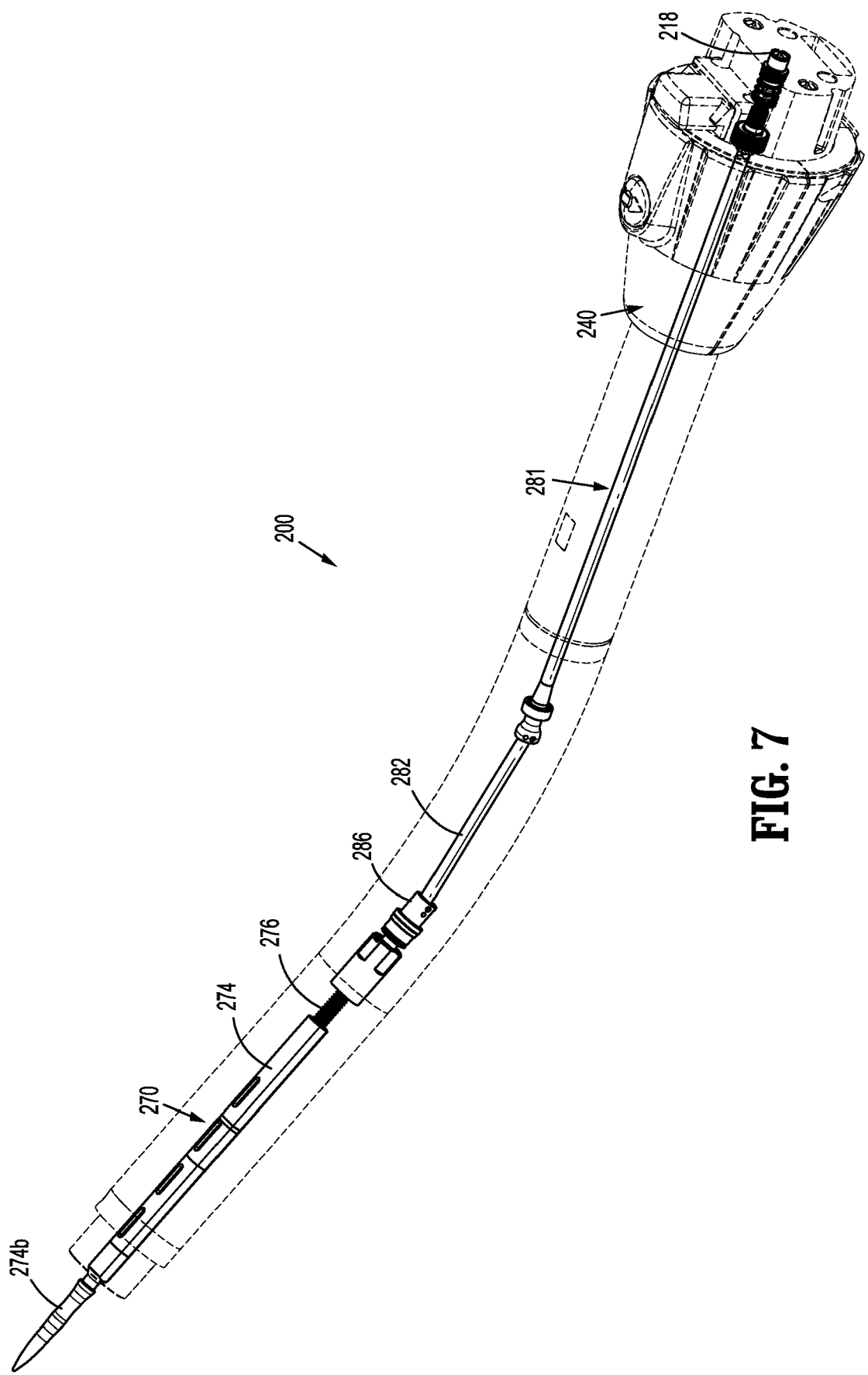
FIG. 7 is a perspective view of the adapter assembly of FIG. 4, shown partially in phantom, illustrating a first force/rotation transmitting/converting assembly thereof.

As shown in FIGS. 6 and 7, the first force/rotation transmitting/converting assembly 240 includes the first rotatable proximal drive shaft 212, as described above, a second rotatable proximal drive shaft 281, a rotatable distal drive shaft 282, and a coupling member 286. The first force/rotation transmitting/converting assembly 240 functions to advance/retract a trocar member 274 of a trocar assembly 270 of the adapter assembly 200, and to open/close the reload 400 (FIG. 1) when an anvil assembly 510 is connected to the trocar member 274.

The trocar assembly 270 is removably supported in a distal end of the outer tube 206 of the adapter assembly 200. The trocar assembly 270 includes an outer housing 272 (not shown) axially and rotationally fixed within the outer tube 206 of the adapter assembly 200, a trocar member 274 slidably disposed within tubular outer housing 272, and a drive screw 276 operably received within the trocar member 274 for axially moving the trocar member 274 relative to the tubular housing 272. A distal end 274b of the trocar member 274 is configured to selectively engage the anvil assembly 510 (FIG. 1).

In operation, as the first rotatable proximal drive shaft 212 is rotated, due to a rotation of the first connector sleeve 218, as a result of the rotation of the first coupling shaft 124a (FIG. 2) of the handle assembly 100, the second rotatable proximal drive shaft 281 is caused to be rotated. Rotation of the second rotatable proximal drive shaft 281 results in contemporaneous rotation of the rotatable distal drive shaft 282. Rotation of the rotatable distal drive shaft 282 causes contemporaneous rotation of the coupling member 286, which, in turn, causes contemporaneous rotation of the drive screw 276 of the trocar assembly 270. As the drive screw 276 is rotated within and relative to the trocar member 274, engagement between the trocar member 274 and the drive screw 276 (e.g., threaded engagement) causes axial translation of the trocar member 274 within the tubular housing 272 of the trocar assembly 270. Specifically, rotation of the drive screw 276 in a first direction causes axial translation of the trocar member 274 in a first direction (e.g., extension or advancement of the trocar assembly 270), and rotation of the drive screw 276 in a second direction causes axial translation of the trocar member 274 in a second direction (e.g., retraction of the trocar assembly 270). When the anvil assembly 510 is connected to the trocar member 274, the axial translation of the trocar member 274 in the first direction results in an opening of the reload 400, and the axial translation of the trocar member 274 in the second direction results in a closing of the reload 400.

Figure 8:
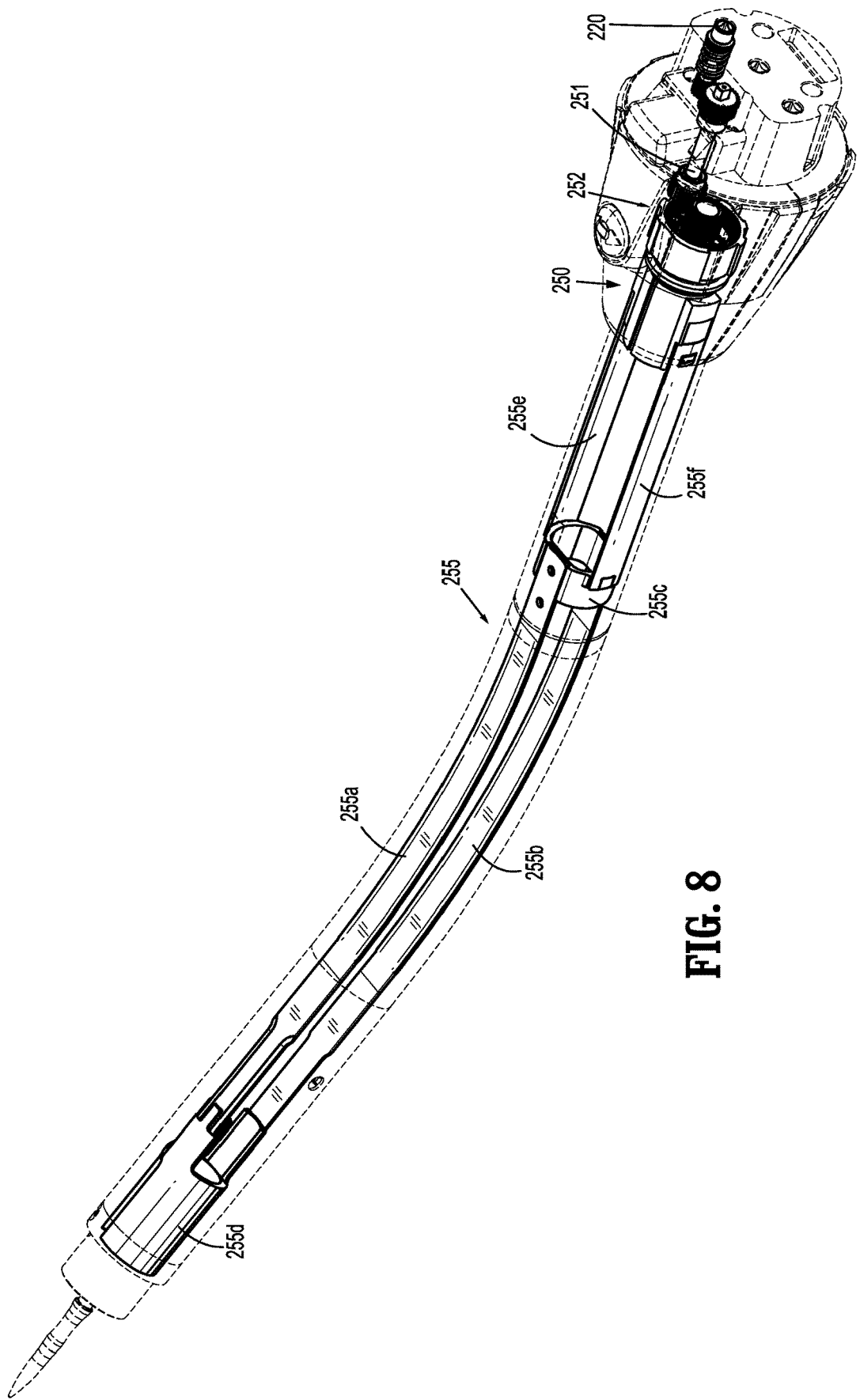
FIG. 8 is a perspective view of the adapter assembly of FIG. 4, shown partially in phantom, illustrating a second force/rotation transmitting/converting assembly thereof.

As shown in FIGS. 6 and 8, the second force/rotation transmitting/converting assembly 250 of adapter assembly 200 includes the second proximal drive shaft 214, as described above, a first coupling shaft 251, a planetary gear set 252, a staple lead screw 253, and a staple driver 254. The second force/rotation transmitting/converting assembly 250 of the adapter assembly 200 also includes an outer flexible band assembly 255 secured to the staple driver 254. The outer flexible band assembly 255 includes first and second flexible bands 255a, 255b laterally spaced and connected at proximal ends thereof to a support ring 255c and at distal ends thereof to a proximal end of a support base 255d. The outer flexible band assembly 255 further includes first and second connection extensions 255e, 255f extending proximally from the support ring 255c that are configured to operably connect the outer flexible band assembly 255 to the staple driver 254. The second force/rotation transmitting/converting assembly 250 functions to fire staples "S" (FIG. 13) of the reload 400 for formation against the anvil assembly 510.

In operation, as the second rotatable proximal drive shaft 214 is rotated due to a rotation of the second connector sleeve 220, as a result of the rotation of the second coupling shaft 124c (FIG. 2) of the handle assembly 100, the first coupling shaft 251 is caused to be rotated, which in turn causes the planetary gear set 252 to rotate. Rotation of the planetary gear set 252 causes contemporaneous rotation of the staple lead screw 253. As the staple lead screw 253 is rotated, the staple driver 254 is caused to be axially translated, which in turn causes the outer flexible band assembly 255 to be axially translated. As the outer flexible band assembly 255 is axially translated, the support base 255d presses against a driver adapter 432 (FIG. 13) of a staple driver assembly 430 of the reload 400 to distally advance a driver 434 and fire staples "S" from a staple cartridge 420 of the reload 400 and against anvil assembly 510 for formation of staples "S" in underlying tissue.

Figure 9:
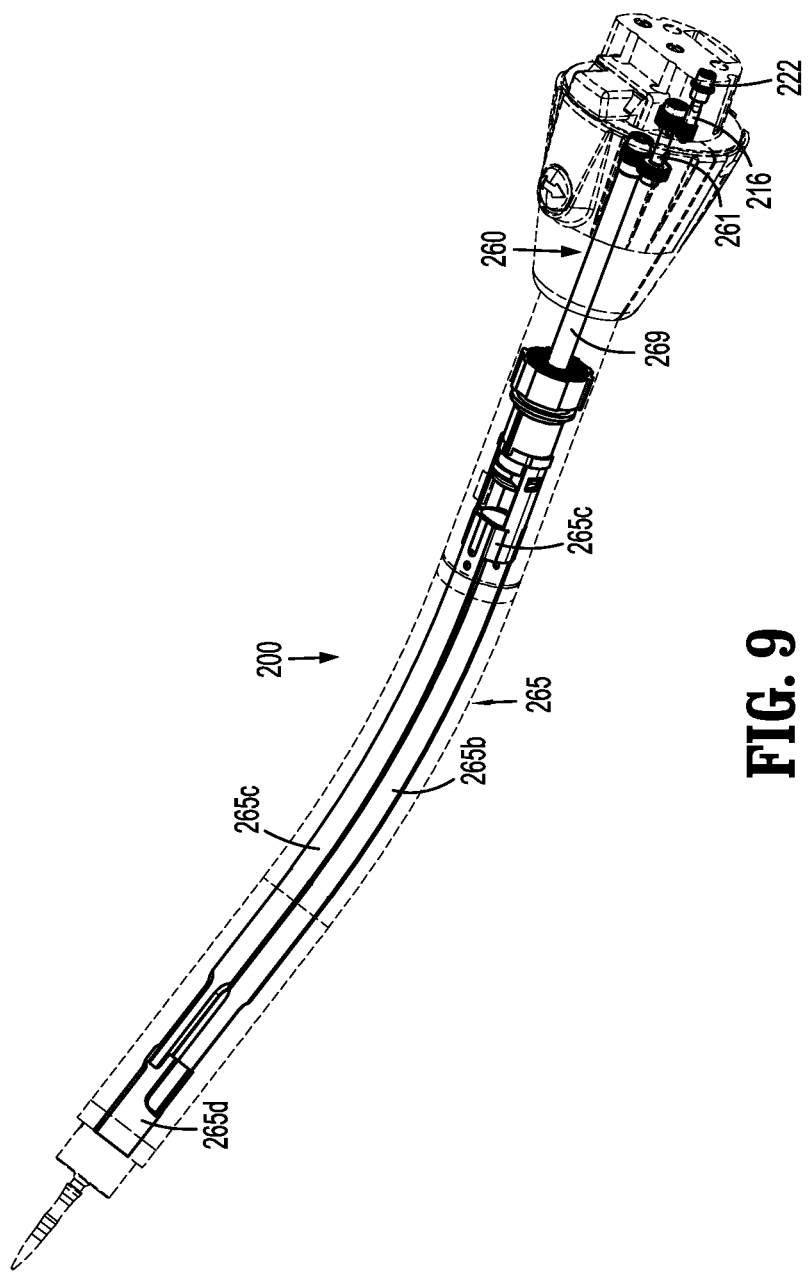
FIG. 9 is a perspective view of the adapter assembly of FIG. 4, shown partially in phantom, illustrating a third force/rotation transmitting/converting assembly thereof.

With reference to FIGS. 6 and 9, the third force/rotation transmitting/converting assembly 260 of the adapter assembly 200 includes the third proximal drive shaft 216, as described above, a second coupling shaft 261, a hollow shaft 269, a planetary gear set 262, a knife lead screw 263, and a knife driver 264. The third force/rotation transmitting/converting assembly 260 of adapter assembly 200 also includes an inner flexible band assembly 265 secured to the knife driver 264. The inner flexible band assembly 265 includes first and second flexible bands 265a, 265b laterally spaced and connected at proximal ends thereof to a support ring 265c and at distal ends thereof to a proximal end of a support base 265d. The third force/rotation transmitting/converting assembly 260 functions to fire an annular knife 444 (FIG. 13) of the reload 400.

In operation, as the third rotatable proximal drive shaft 216 is rotated due to a rotation of the third connector sleeve 222, as a result of the rotation of the third coupling shaft 124b (FIG. 2) of the handle assembly 100, the second coupling shaft 261 is caused to be rotated, which in turn causes the hollow shaft 269 to rotate. Rotation of the hollow shaft 269 results in contemporaneous rotation of the planetary gear set 262, which in turn causes the knife lead screw 263 to rotate. As the knife lead screw 263 is rotated, the knife driver 264 is caused to be axially translated, which in turn causes the inner flexible band assembly 265 to be axially translated. As the inner flexible band assembly 265 is axially translated, the support base 265d presses against a knife carrier 442 (FIG. 13) of the reload 400 to distally advance the knife carrier 442 and fire the annular knife 444 of the reload 400 against the anvil assembly 510 for cutting of tissue clamped in the reload 400.

Figure 10:
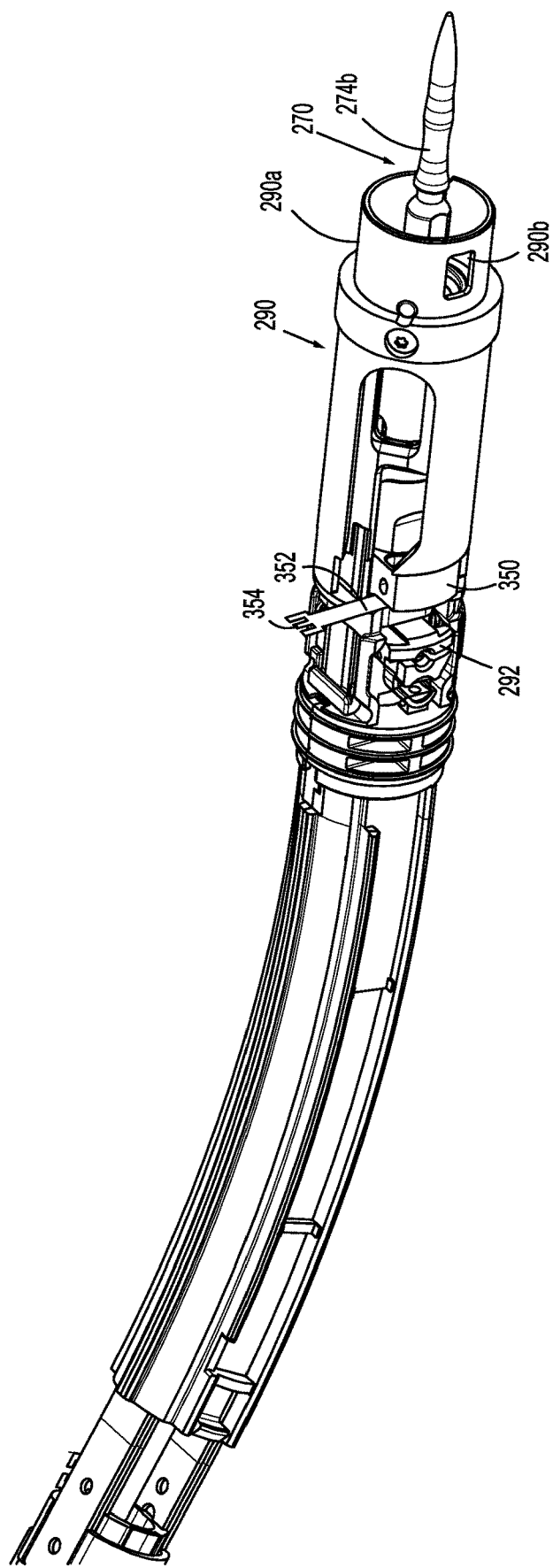
FIG. 10 is a perspective view of the adapter assembly of FIG. 4, with an outer tube of the adapter assembly removed, illustrating internal components of a distal portion of the adapter assembly.

With reference now to FIG. 10, a strain sensor 350 is supported in the outer tube 206 (FIG. 4) of the adapter assembly 200. The strain sensor 350 is interposed between the connector sleeve 290 and a support block 292, and defines a lumen (not shown) therethrough, through which the trocar assembly 270 extends. A sensor flex cable 352 is electrically coupled to the strain sensor 320 and terminates at an electrical connector 354 (e.g., a female connector). As seen in FIG. 4, the electrical connector 354 is secured within the outer tube 206 of the adapter assembly 200 for electrical connection with the electrical assembly 300 (FIG. 18), as will be described in further detail below. Alternatively, the strain sensor 350 may be electrically coupled to the electrical connector 354 via insulated wires, such as PEEK insulated wires, having a potting compound along the connection points to withstand cleaning and sterilization processes. Other methods are within the purview of those skilled in the art for connecting the strain sensor 350 to the electrical connector 354 to form a permanent and cleanable/sterilizable connection.

Forces, for example, during an actuation of the trocar member 274 or a closing of the reload 400, may be measured by the strain sensor 350. The strain sensor 350 is configured to measure strain (a dimensionless quantity) on an object that it is adhered to (e.g., the support block 292), such that, as the object deforms, a metallic foil of the strain sensor 350 is also deformed, causing an electrical resistance thereof to change, which change in resistance is then used to calculate loads experienced by the trocar assembly 270.

The strain sensor 350 then communicates signals to the main controller circuit board 142b (FIG. 2) of the power-pack core assembly 130 of the handle assembly 100 via the electrical assembly 300 (FIG. 19). Graphics are then displayed on the display screen 134 of the power-pack core assembly 130 to provide the user with real-time information related to the status of the firing of the handle assembly 100.

For a detailed description of the structure and function of exemplary strain sensors, reference may be made to commonly owned U.S. Patent Appl. Pub. No. 2018/0067004, the entire content of which is incorporated herein by reference.

Figure 11:
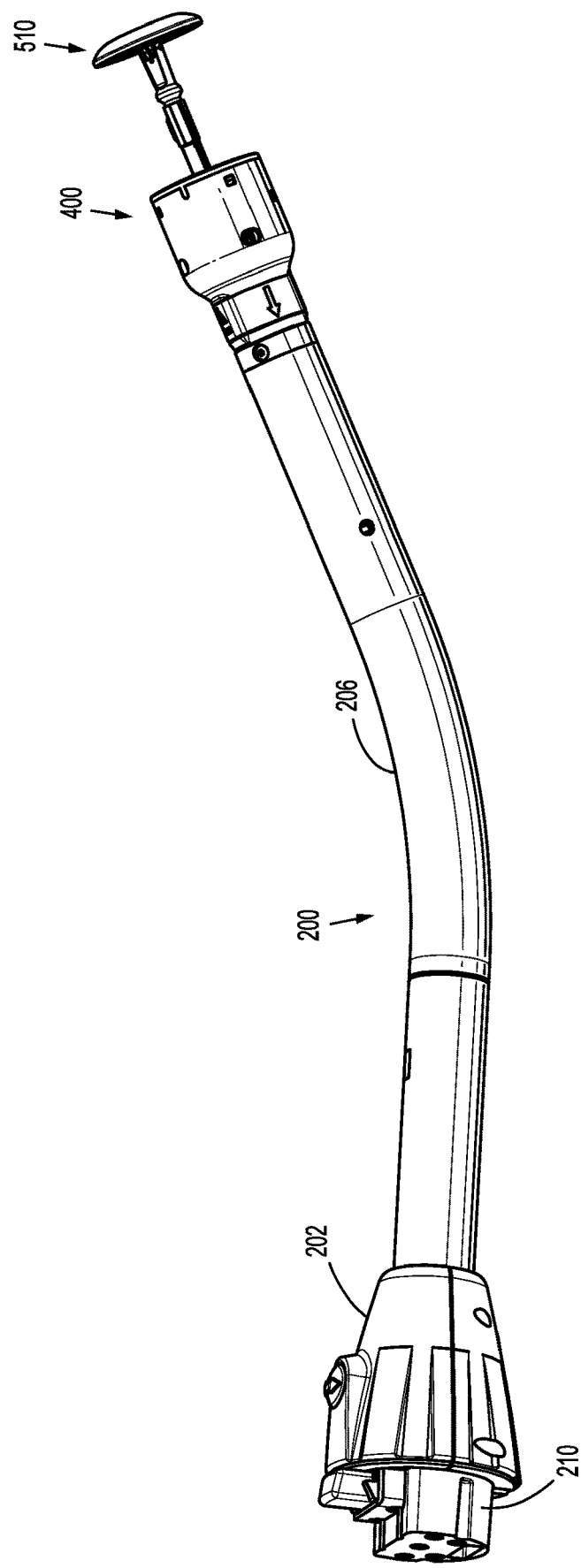
FIG. 11 is a perspective view of the adapter assembly, illustrating a reload secured to a distal end thereof.
Figure 12:
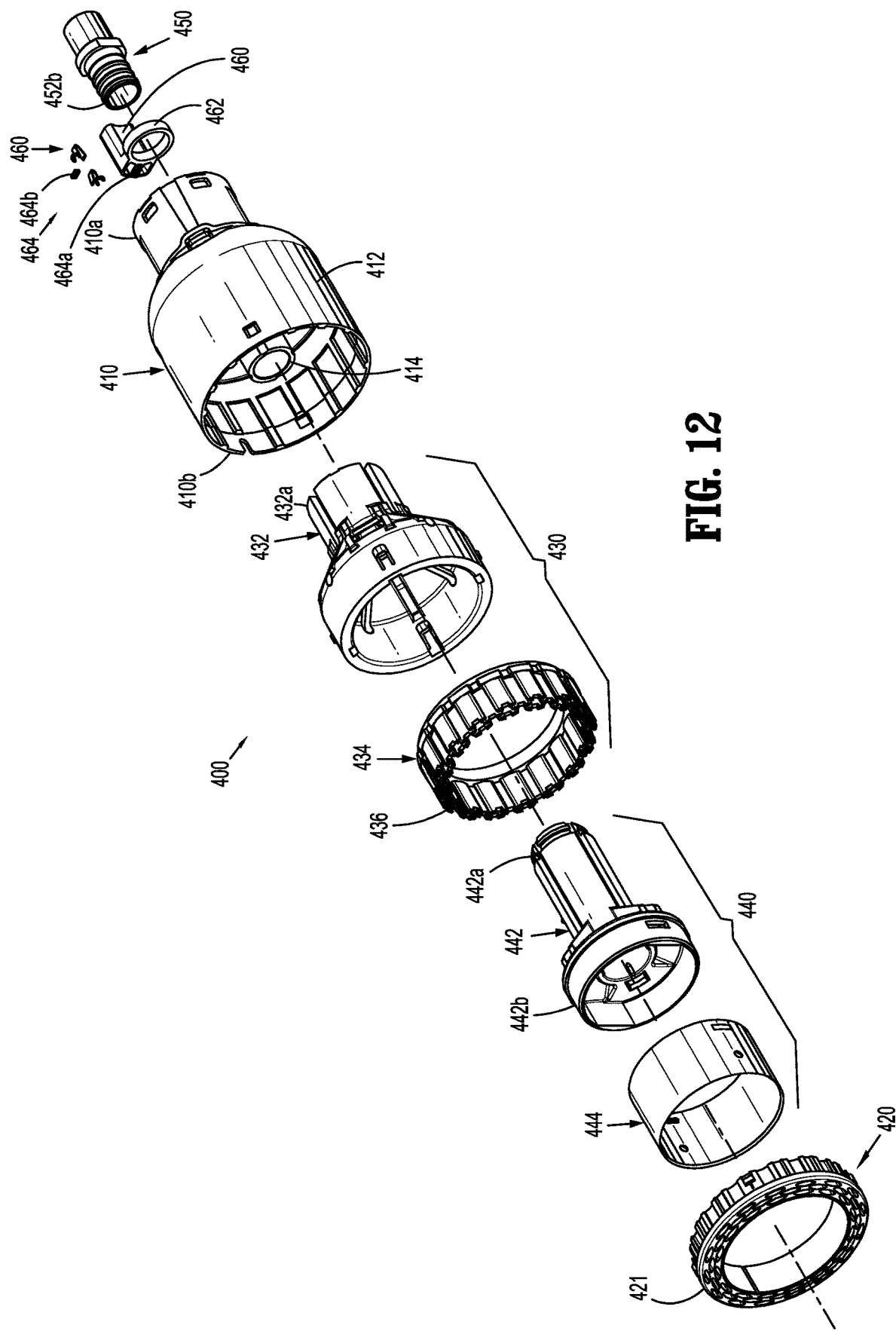
FIG. 12 is a perspective view, with parts separated, of the reload of FIG. 11.
Figure 13:
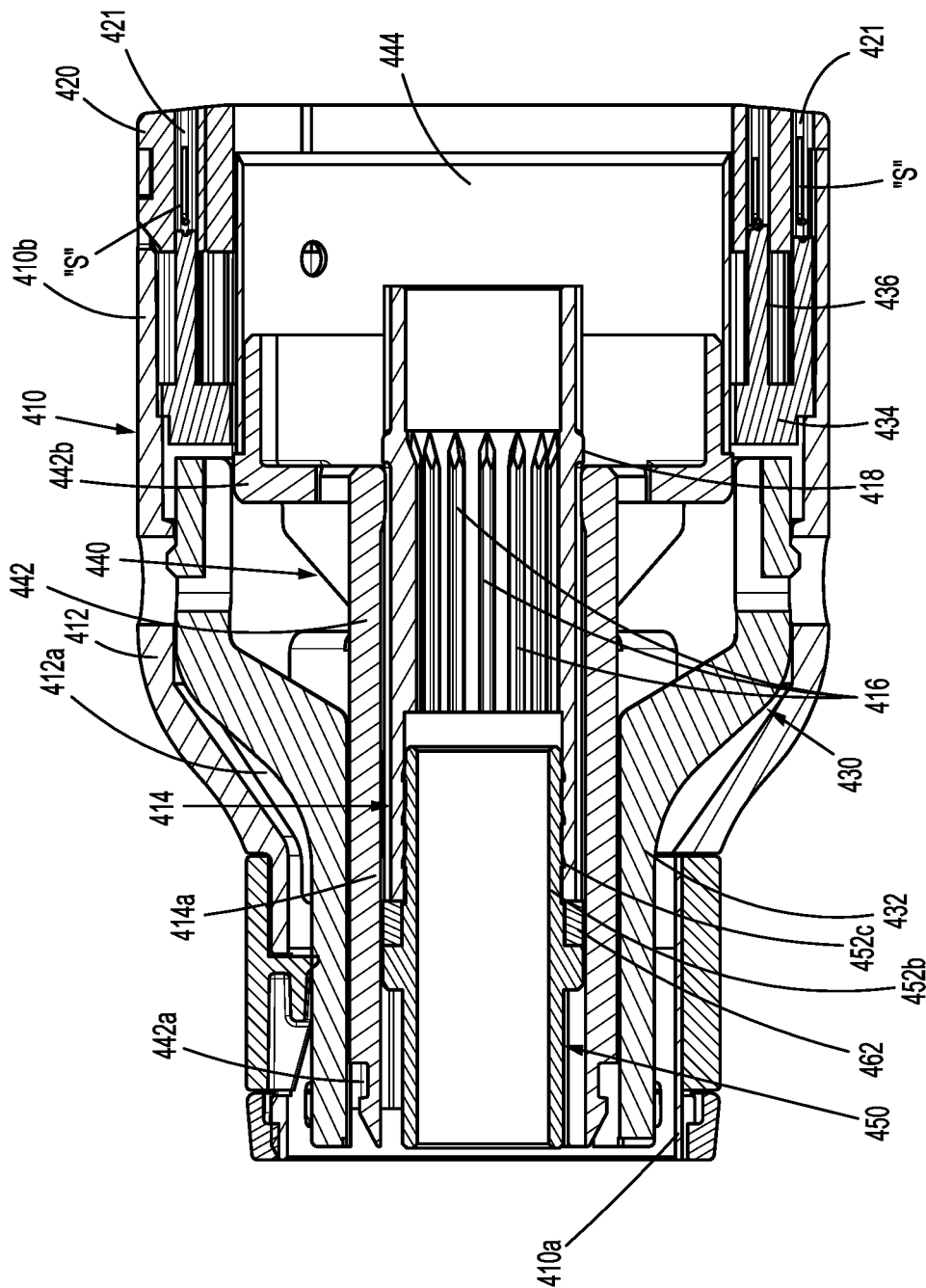
FIG. 13 is a longitudinal, cross-sectional view of the reload of FIG. 12.

Turning now to FIG. 11, the reload 400 is configured for operable connection to the adapter assembly 200 and is configured to fire and form an annular array of surgical staples, and to sever a ring of tissue. As illustrated in FIGS. 12 and 13, the reload 400 includes a housing 410 having a proximal end portion 410a and a distal end portion 410b, a staple cartridge 420 fixedly secured to distal end portion 410b of the housing 410, a staple driver assembly 430 operably received within the housing 410, a knife assembly 440 operably received within the housing 410, a bushing member 450 received within the proximal end 410a of the housing 410, and a chip assembly 460 mounted about the bushing member 450.

The reload 400 may include a shipping cap assembly (not shown) that is selectively received on a distal end of the reload 400 and can function to maintain staples "S" within the staple cartridge 420 of the reload 400 and to prevent premature advancement of the staple driver assembly 430 and the knife assembly 440 of the reload 400 prior to and during attachment of the reload 400 to the adapter assembly 200.

With continued reference to FIGS. 12 and 13, the housing 410 of the reload 400 includes an outer cylindrical portion 412 and an inner cylindrical portion 414 that are interconnected by a plurality of ribs (not shown). The outer cylindrical portion 412 and the inner cylindrical portion 414 of the reload 400 are coaxial and define a recess 412a therebetween configured to operably receive the staple driver assembly 430 and the knife assembly 440. The inner cylindrical portion 412 of the reload 400 includes a plurality of longitudinally extending ridges 416 projecting from an inner surface thereof and configured for radially aligning (e.g., clocking) the anvil assembly 510 (FIG. 11) with the reload 400 during a stapling procedure. An annular ridge 418 is formed on an outer surface of the inner cylindrical portion 412 and is configured to assist in maintaining the knife assembly 440 in a retracted position.

The staple cartridge 420 of the reload 400 is fixedly secured on the distal end 410b of housing 410 and includes a plurality of staple pockets 421 formed therein which are configured to selectively retain staples "S".

The staple driver assembly 430 of the reload 400 includes a driver adapter 432 and a driver 434. A proximal end 432a of the driver adapter 432 is configured for selective contact and abutment with the support base 255d (FIG. 8) of the outer flexible band assembly 255 of second force/rotation transmitting/converting assembly 250 of the adapter assembly 200. In operation, during distal advancement of the outer flexible band assembly 255, as described above, the support base 255d of the outer flexible band assembly 255 contacts the proximal end 432a of the driver adapter 432 to advance the driver adapter 432 and the driver 434 from a first or proximal position to a second or distal position. The driver 434 includes a plurality of driver members 436 aligned with the plurality of staple pockets 421 of the staple cartridge 420 for contact with staples "S". Accordingly, advancement of the driver 434 relative to the staple cartridge 420 causes ejection of the staples "S" from the staple cartridge 420.

The knife assembly 440 of the reload 400 includes a knife carrier 442 and a circular knife 444 secured about a distal end 442b of the knife carrier 442. A proximal end 442a of the knife carrier 442 is configured for operable connection with the support base 265d (FIG. 9) of the inner flexible band assembly 265 of the third force/rotation transmitting/converting assembly 260 of the adapter assembly 200. In operation, during distal advancement of the inner flexible band assembly 265, as described above, the support base 265d of the inner flexible band assembly 265 connects with the proximal end 442a of the knife carrier 442 to advance the knife carrier 442 and the circular knife 444 from a first or proximal position to a second or advanced position to cause the cutting of tissue disposed between the staple cartridge 420 and the anvil assembly 510.

The distal end 452b of the bushing member 450 is secured within a proximal end 414a of the inner cylindrical portion 414 of the housing 410 by a plurality of ridges 452c formed on the distal end 452b of the bushing member 450. The chip assembly 460 includes a housing 461 from which annular flange 462 extends. The annular flange 462 extends perpendicular to a longitudinal axis of the housing 461. The annular flange 462 is configured to be received about the distal end 452b of the bushing member 450.

The chip assembly 460 includes a circuit board assembly 464 secured within a cavity 461a of housing 461. The circuit board assembly 464 includes a circuit board 464a and a chip 464b. The chip 464b is a writable/erasable memory chip including the following stored information: lot number, staple size, lumen size, fire count, manufacturing stroke offsets, excessive force index, shipping cap assembly presence, and demonstration modes. The chip 464b includes write capabilities which allow the handle assembly 100 to encode to the chip 464c that the reload 400 has been used to prevent reuse of an empty, spent or fired reload.

Figure 14:
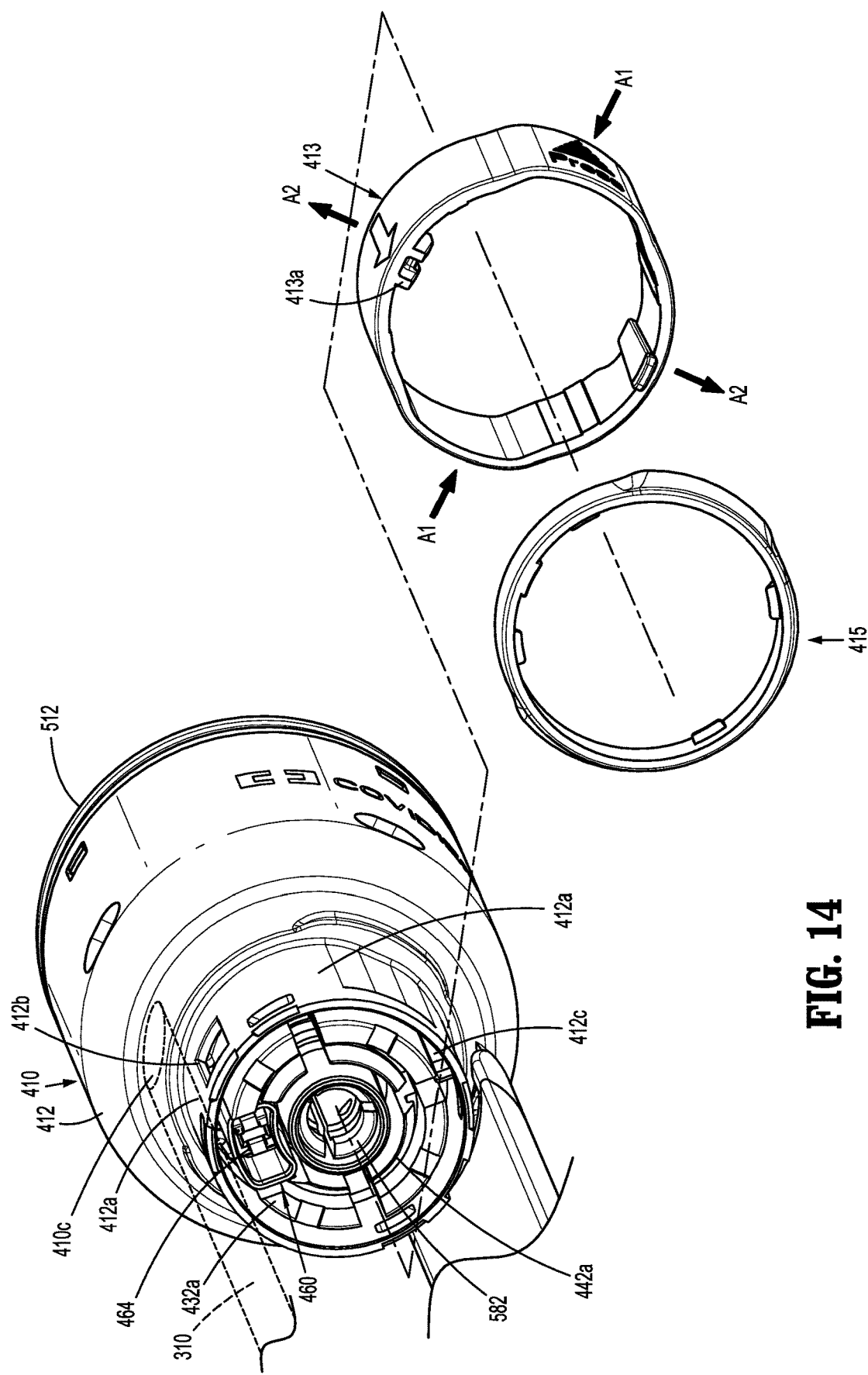
FIG. 14 is a rear, perspective view of the reload of FIG. 12, with a release ring and a retaining ring illustrated separated therefrom.

As shown in FIG. 14, the proximal end 410a of the housing 410 is configured for selective connection to the connector sleeve 290 (FIG. 10) of the adapter assembly 200. Specifically, the outer cylindrical portion 412 of the housing 410 terminates in a proximal cylindrical flange 412a having an inner diameter which is larger than a diameter of a distal end portion 290a of the connector sleeve 290 of the adapter assembly 200. Further, the proximal end 432a of the driver adapter 432 has an outer diameter which is smaller than the diameter of the distal end portion 290a of the connector sleeve 290.

The reload 400 includes a compressible release ring 413 supported on the flange 412a of the outer cylindrical portion 412 of the housing 410, and a retaining ring 415 connected to the outer cylindrical portion 412 of the housing 410 and configured to help retain the release ring 413 on the outer cylindrical portion 412 of the housing 410. During connection of the reload 400 with the adapter assembly 200, the reload 400 and the adapter assembly 200 are axially approximated towards one another until the distal end portion 290a (FIG. 10) of the connector sleeve 290 is received within the flange 412a of the outer cylindrical portion 412 of the housing 410 and until a ramp feature 413a of the release ring 413 is received in a window 290b of the connector sleeve 290. The reload 400 and the adapter assembly 200 are thus locked together. To disconnect the reload 400 and the adapter assembly 200 from one another, the release ring 413 is squeezed along the long axis thereof (in the direction of arrows "A1") such that the release ring 413 flexes radially outwardly along the short axis thereof (in the direction of arrows "A2") to thereby remove the ramp feature 413a of the release ring 413 from within the window 290b of the connector sleeve 290, and thus allowing the reload 400 and the adapter assembly 200 to be axially separated from one another.

A flex cable 310 (shown in phantom) of an electrical assembly 300 extends through a port 410c defined in the housing 410 of the reload 400. The flex cable 310 is electrically coupled to the circuit board assembly 464 of the chip assembly 460 of the reload 400, as described in further detail below.

Figure 15:
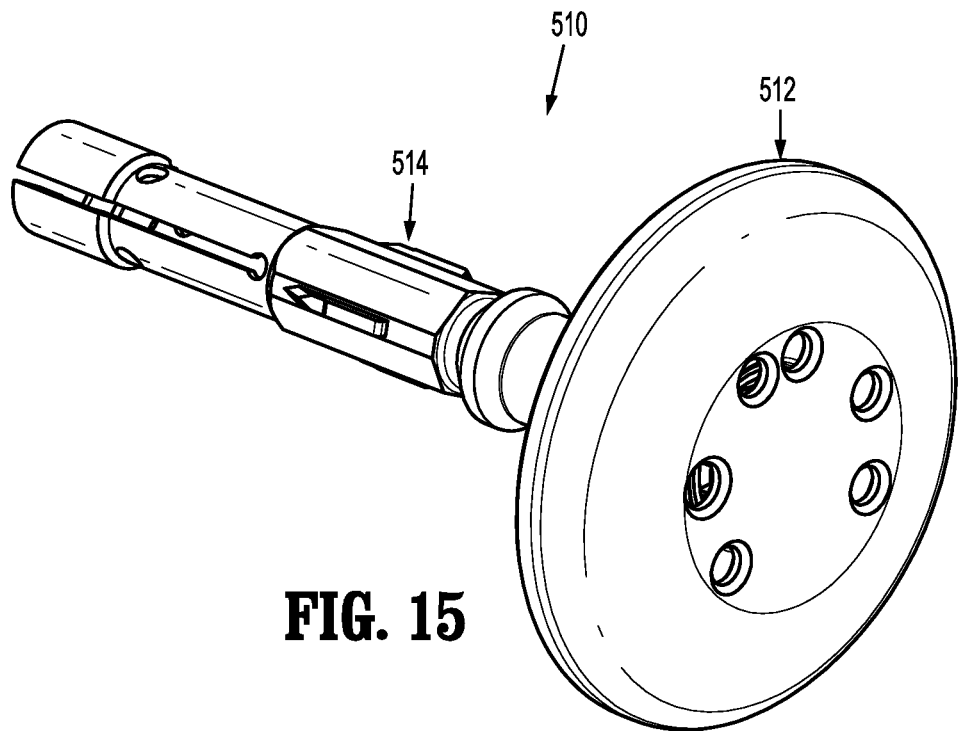
FIG. 15 is a front, perspective view of an anvil assembly of the end effector of FIG. 1.
Figure 16:
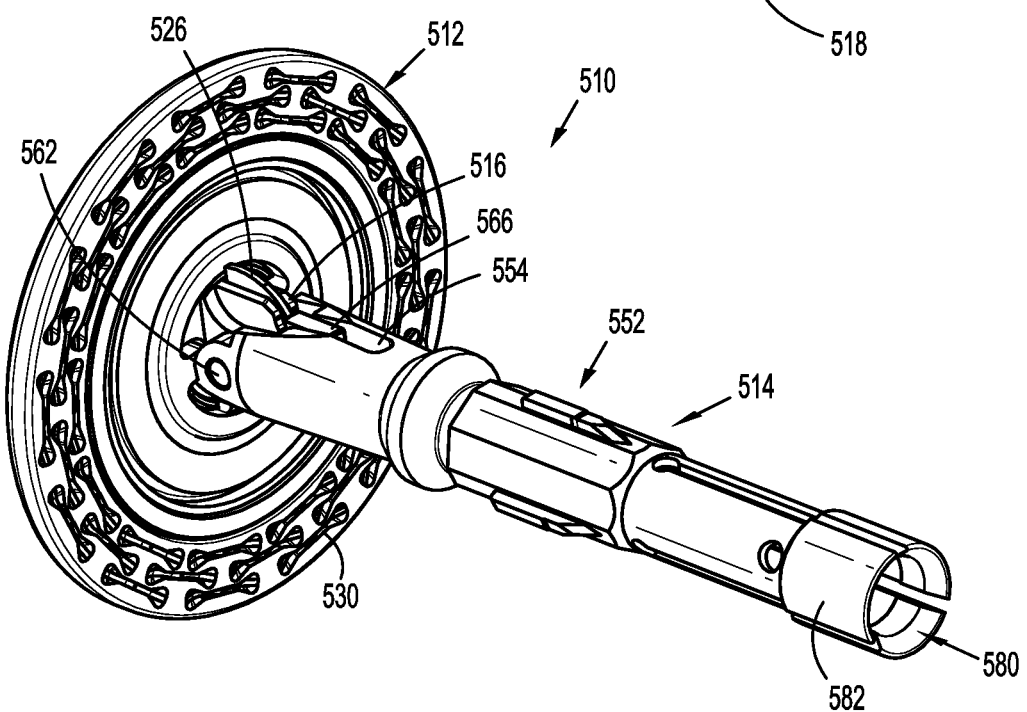
FIG. 16 is a rear, perspective view of the anvil assembly of FIG. 15.
Figure 17:
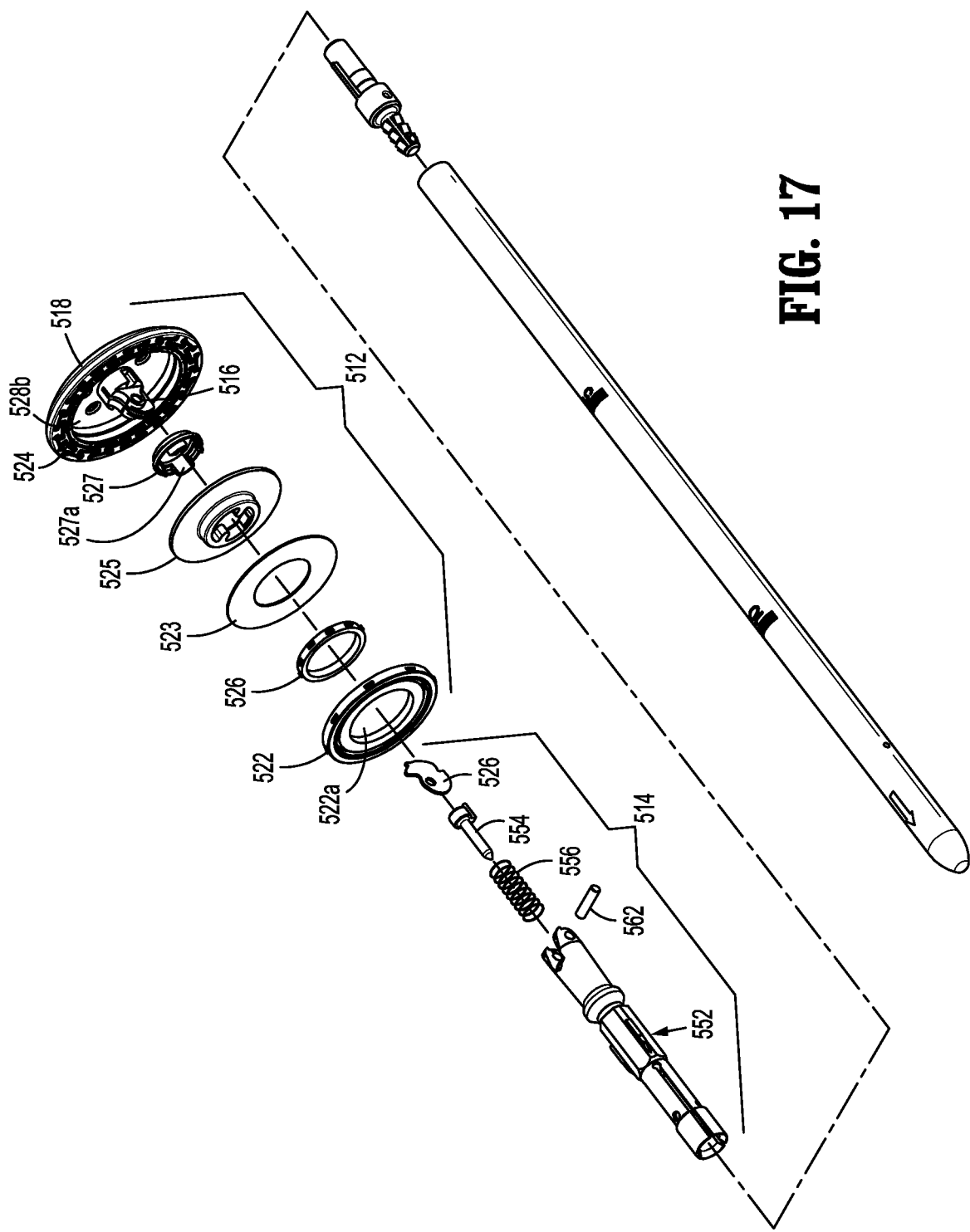
FIG. 17 is a perspective view, with parts separated, of the anvil assembly of FIG. 15.

Referring now to FIGS. 15-17, an anvil assembly 510 is provided and is configured for selective connection to the trocar member 274 of the adapter assembly 200 and for cooperation with the reload 400. The anvil assembly 510 includes a head assembly 512 and a center rod assembly 514. The head assembly 512 includes a post 516, a housing 518, a cutting ring 522, a cutting ring cover 523, an anvil plate 524, a spacer or washer 525, a cam latch member 526, and a retainer member 527. The post 516 is centrally positioned within the housing 518.

The anvil plate 524 is supported in an outer annular recess (not explicitly shown) of the housing 518 and includes a plurality of staple pockets 530 formed therein that are configured to receive and form staples. The cutting ring 522 includes a central opening 522a which is positioned about the post 516 within an inner annular recess 528b of the housing 518. The cutting ring cover 523 is secured to an outwardly facing or proximal surface of the cutting ring 522.

The retainer member 527 is positioned in the inner annular recess 528b of the housing 518 between the cutting ring 522 and a back wall of the housing 518. The retainer member 527 is annular and includes a plurality of deformable tabs 527a which engage a rear surface of the cutting ring 522. The retainer member 527 prevents the cutting ring 522 from moving or being pushed into the inner annular recess 528b of the housing 518 until a predetermined force sufficient to deform the tabs 527a has been applied to the cutting ring 522. When the predetermined force is reached, e.g., during cutting of tissue, the cutting ring 522 is urged into the inner annular recess 528b and compresses the retainer member 527.

The anvil center rod assembly 514 includes a center rod 552, a plunger 554, and a plunger spring 556. A pivot member 562 is provided to pivotally secure the post 516 of the housing 518 to the center rod 552 such that the anvil head assembly 512 is pivotally mounted to the anvil center rod assembly 514.

A cam latch member 526 is pivotally mounted within a transverse slot of the post 516 of the housing 518 and about the pivot member 562. The cam latch member 526 has an outer cam profile which permits the plunger 554 to move forward as the cam latch member 526 rotates in a clockwise direction, and permits the plunger 554 to be retracted as cam latch member 526 rotates in a counter-clockwise direction.

The plunger 554 is slidably positioned in a bore formed in the first end of the center rod 552. The plunger 554 includes an engagement finger 566 which is offset from the pivot axis of the anvil head assembly 512 and biased into engagement with an edge of the cam latch 526. Engagement of the finger 566 of the plunger 554 with the edge of the cam latch 526 presses a leading portion of the edge of the cam latch 526 against an inner periphery of the cutting ring 522 to urge the anvil head assembly 512 to an operative or non-tilted position on the center rod 552.

The anvil head assembly 512 may be tilted relative to the anvil center rod assembly 514 in a pre-fired tilted position. Tilting of the anvil head assembly 512 relative to the anvil center rod assembly 514 causes the body portion of the cam latch member 526 to engage the finger 566 of the plunger 554. As the cam latch member 526 rotates with the tilting of the anvil head assembly 512, the plunger 554 is retracted with the bore of the anvil center rod assembly 514, thereby compressing the spring 556. In this manner, the finger 566 of the plunger 554 is distally biased against the body portion of the cam latch member 526.

A second end of the center rod 552 includes a bore 580 defined by a plurality of flexible arms 582. The proximal end of each of the flexible arms 582 includes an internal shoulder dimensioned to releasably engage a shoulder of the trocar 274 (FIG. 7) of the trocar assembly 270 of the adapter assembly 200 to secure the anvil assembly 510 to the adapter assembly 200.

With reference now to FIG. 18, an electrical assembly 300 extends proximally from the reload 400 and is configured to enable communication between the handle assembly 100, the adapter assembly 200, and the reload 400 of the surgical device 1. For example, this communication allows for calibration and communication of data and control signals between the reload 400 and the adapter assembly 200, as well as between the adapter assembly 200 and the handle assembly 100, thereby transferring data pertaining to the reload 400 to the handle assembly 100 and signals from the handle assembly 100 to the reload 400. The electrical assembly 300 serves to allow for calibration and communication of information (e.g., identifying information, life-cycle information, system information, force information) to the main controller circuit board 142b of the power-pack core assembly 130 via the electrical receptacle 149 of the power-pack core assembly 130 of the handle assembly 100 (FIG. 2).

The electrical assembly 300 includes at least one flex cable 310 having an elongate body or substrate 312 suitable for supporting and/or electrically connecting electronic components thereto. The electronic components may be, for example, surface mount technology and/or through-hole technology, including, for example, integrated circuits (e.g., microchips, microcontrollers, microprocessors), resistors, amplifiers, inductors, capacitors, sensing elements (e.g., optical sensors, pressure sensors, capacitive sensors), buttons, switches, circuit boards, electrical connectors, cables, and/or wires, among other elements or circuitry within the purview of those skilled in the art.

The substrate 312 of the flex cable 310 is formed from one or more sheets of dielectric material, such as a polymer or a ceramic, and one or more layers of conductive material, such as copper foil, that form conductive traces (not explicitly shown) in the substrate 312. Vias (not shown) may interconnect the conductive traces through different layers of the flex cable 310.

The flex cable 310 includes a proximal portion 310a and a distal portion 310b. The proximal portion 310a terminates at a proximal end 310c that is electrically coupled to a pin connector assembly 320. The pin connector assembly 320 includes a plurality of electrical contact blades 322 supported on a circuit board 324. The pin connector assembly 320 is positionable within the cavity 211 (shown in phantom) defined in the drive coupling assembly 210 of the adapter assembly 200 such that the pin connector assembly 320 is supported therein.

Figure 20:
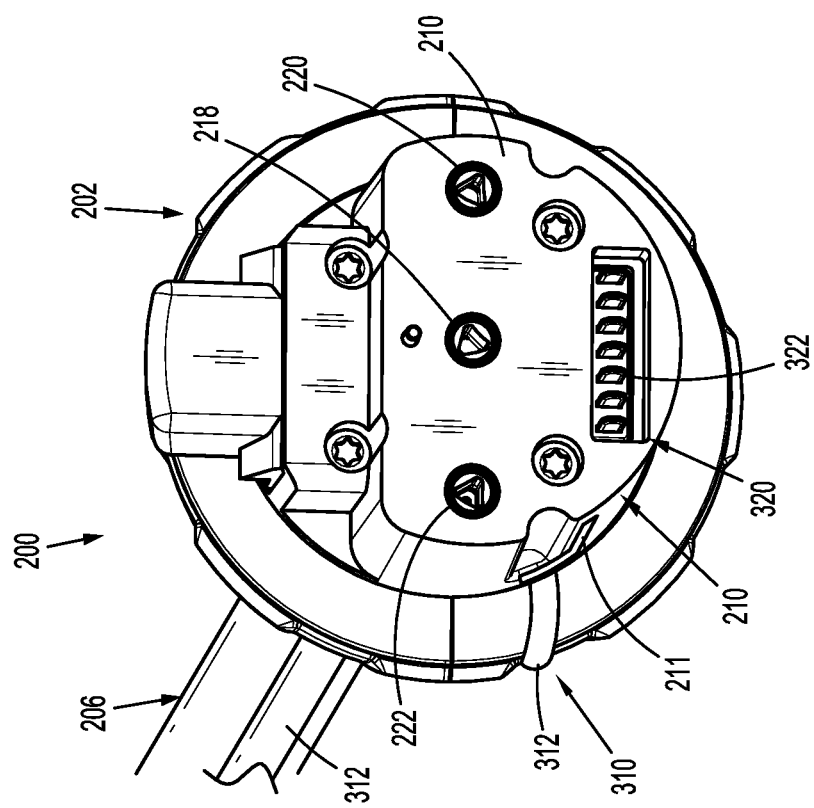
FIG. 20 is an end view of the adapter assembly and the end effector of FIG. 19.

As shown in FIGS. 18-20, the pin connector assembly 320 is slidable into the cavity 211 of the drive coupling assembly 210 of the adapter assembly 200 such that the printed circuit board 324 fits within the guiding ribs 211a of the cavity 211 and the electrical contact blades 322 are disposed or situated within the drive coupling assembly 210 to electrically and/or mechanically engage respective corresponding features of the handle assembly 100 (FIG. 1). The pin connector assembly 320 is configured to interface with the handle assembly 100 by enabling electrical connection to the pass-through connector 126 (FIG. 2) of the plate assembly 120 of the shell housing 110 of the handle assembly 100.

The distal portion 310b of the flex cable 310 terminates at a distal end 310d (shown in phantom) that is electrically coupled to the circuit board assembly 464 (shown in phantom) of the reload 400. The distal end 310d of the flex cable 310 is permanently attached to the circuit board assembly 464 (e.g., via a solder connection) and the flex cable 310 extends through the port 410c defined in the housing 410 of the reload 400 proximally away therefrom. Alternatively, an electrical connector (not shown) may be electrically coupled to the distal end 310d of the flex cable 310 such that the flex cable 310 is releasably connectable to the circuit board assembly 464 of the reload 400.

The flex cable 310 is of sufficient length such that when the reload 400 is secured to the adapter assembly 200, the pin connector assembly 320 can be positioned within the drive connector assembly 210 of the knob housing 202 of the adapter assembly 200. The flex cable 310 may include an adhesive (not explicitly shown) disposed along the length or portions of the length thereof, on a first side 312a of the substrate 312 of the flex cable 310 positionable against the adapter assembly 200 to help retain the flex cable 310 thereto. For example, a release liner may be disposed over the adhesive and removed prior to coupling the reload 400 to the adapter assembly 200 to help retain the flex cable 310 thereto.

The flex cable 310 includes a strain sensor electrical connector 330 electrically coupled thereto. The strain sensor electrical connector 330 is disposed in a position along the length of the flex cable 310 that is aligned with the electrical connector 354 secured within the outer tube 206 of the adapter assembly 200, as described above. The strain sensor electrical connector 330 is a plug (e.g., a male connector) and the electrical connector 354 is a jack (e.g., a female connector) that electrically interconnect the strain sensor 350 of the adapter assembly 200 with the electrical assembly 300 when the strain sensor electrical connector 330 is inserted into the electrical connector 354. It should be understood that the strain sensor electrical connector 330 and the electrical connector 354 may have any complementary or mating configurations for forming an electrical connection therebetween.

The flex cable 310 further includes a printed circuit board 340 disposed or integrated thereon including circuitry for functioning of the adapter assembly 200 as described above. The printed circuit board 340 is positioned along the proximal portion 310a of the flex cable 310 and is aligned with the knob housing 202 of the adapter assembly 200. An adhesive (not shown) may be disposed between the printed circuit board 340 and the adapter assembly 200 to help retain the printed circuit board 340 thereon. It should be understood that the printed circuit board 340 may be positioned along any portion of the length of the flex cable 310 and/or the flex cable 310 may include a plurality of printed circuit boards 340 integrated or disposed thereon.

Figure 21:
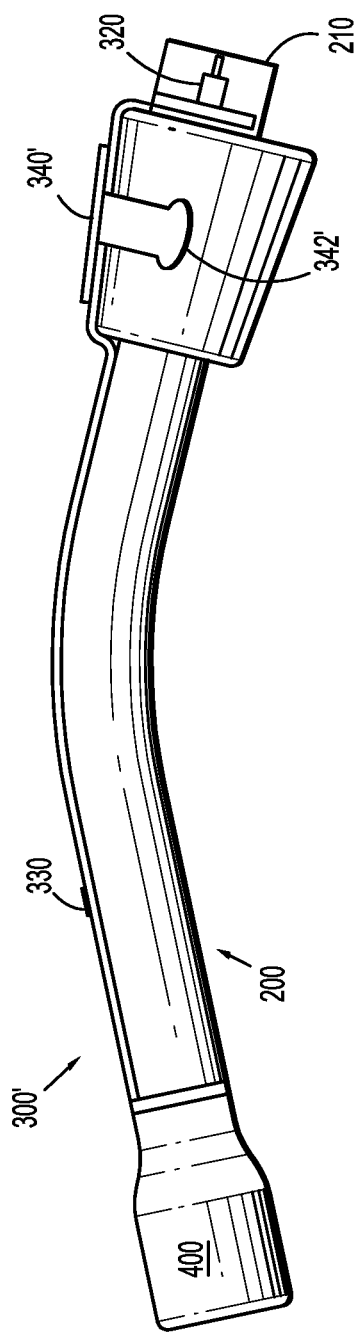
FIG. 21 is a side view of an anvil assembly and an end effector in accordance with another embodiment of the present disclosure.
Figure 22:
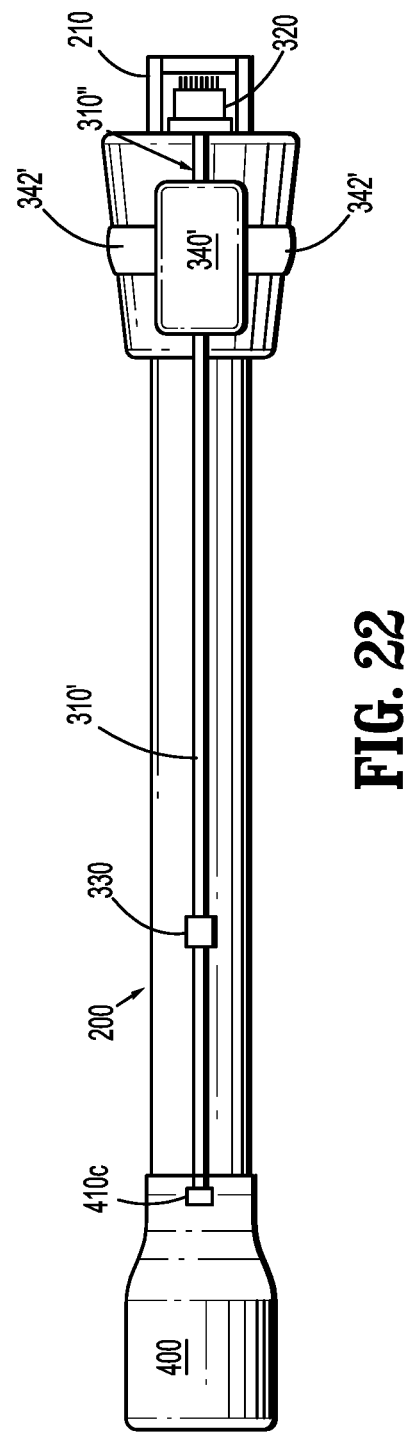
FIG. 22 is a side view of the anvil assembly and the end effector of FIG. 21.

FIGS. 21 and 22 illustrate an electrical assembly 300' in accordance with another embodiment of the present disclosure. The electrical assembly 300' is substantially similar to the electrical assembly 300 and will be described with respect to the differences therebetween. The electrical assembly 300' includes a proximal flex cable 310', a distal flex cable 310", a pin connector assembly 320, a strain sensor electrical connector 330, and a printed circuit board 340'.

The printed circuit board 340' may be a flexible or rigid printed circuit board electrically coupled to the proximal flex cable 310' and the distal flex cable 310". The proximal flex cable 310' is also electrically coupled to the pin connector assembly 320, and the distal flex cable 310" is electrically coupled to the strain sensor electrical connector 330 and the circuit board assembly 464 (FIG. 18) of the reload 400. Attaching portions or wings 342' extend laterally from the printed circuit board 340' and include an adhesive (not explicitly shown) for releasably securing the printed circuit board 340' to the adapter assembly 200.

In a method of operation, in accordance with an embodiment of the present disclosure, after the power handle 101 is enclosed within the shell housing 110 to form the handle assembly 100, the pin connector assembly 320 of the electrical assembly 300 is inserted into the drive coupling assembly 210 of the adapter assembly 200 and the strain sensor electrical connector 330 is mated with the electrical connector 354 of the adapter assembly 200, as described above. The adapter assembly 200 is then coupled to handle assembly 100. The handle assembly 100 verifies that the adapter assembly 200 is coupled thereto and authenticates and calibrates the adapter assembly 200.

After the adapter assembly 200 is calibrated, the reload 400, which may include a shipping cap assembly, is coupled to the adapter assembly 200 and the flex cable 310 of the electrical assembly 300 may be secured to the knob housing 202 or the outer tube 206 of the adapter assembly 200, as described above. The handle assembly 100 verifies that reload 400 is attached to adapter assembly 200 by establishing communications with the chip 464c of the reload 400. The handle assembly 100 also authenticates the chip 464c and confirms that reload 400 has not been previously fired.

Alternatively, the electrical assembly 300 and the reload 400 may be secured to the adapter assembly 200 prior to coupling the adapter assembly 200 to the handle assembly 100 such that the handle assembly 100 verifies, authenticates, and calibrates the adapter assembly 200 and then the reload 400.

Upon attaching the reload 400 and confirming that the reload 400 is unused and has been authenticated, the handle assembly 100 prompts the user to eject the shipping cap assembly. After the shipping cap assembly is ejected, the handle assembly 100 is ready for use.

The user commences a surgical procedure which includes preparing the target tissue area and positioning the surgical device within a tissue (e.g., the colorectal or upper gastrointestinal region) or until the trocar member 274 of the adapter assembly 200 extends sufficiently to permit piercing of tissue. After extension of the trocar member 274, the anvil assembly 510 (already positioned by the user) is attached to the trocar member 274 and the user begins the clamping process (on the tissue interposed between the reload 400 and the anvil assembly 510).

During the clamping process, the main controller of the handle assembly 100 commences a controlled tissue compression ("CTC") algorithm which varies the clamping speed during tissue compression without exceeding a target compression force. The distance at which the controller commences the CTC corresponds to the distance at which the anvil assembly 510 begins to compress the tissue against the staple guide of the reload 400 for the remainder of the clamping process. CTC continues until a predetermined gap distance between the anvil assembly 510 and the reload 400 has been reached. During CTC, the strain sensor 350 continuously provides measurements to the main controller of the handle assembly 100 via the electrical assembly 300 on the force imparted on the first rotation transmitting assembly 240 as it moves the anvil assembly 510.

Once the CTC algorithm is complete and tissue is compressed, stapling mode can be initiated. During the stapling sequence, the second rotation transmitting assembly 250 is moved to convert rotation to linear motion and to eject and form staples "S" from the reload 400. During the firing sequence, the force imparted on the second rotation transmitting assembly 250 is monitored by the strain sensor 350 to ensure that maximum force limit is not exceeded. The process is deemed complete once the second rotation transmitting assembly 250 reaches a hard stop corresponding to a force threshold detected by the strain sensor 350. This indicates that the staples "S" have been successfully ejected and deformed against the anvil assembly 510.

Once the stapling sequence is complete, the surgical device 10 automatically commences the cutting sequence. During the cutting sequence, the force imparted on the third rotation transmitting assembly 260 is monitored by the strain sensor 350 to ensure that maximum force limit is not exceeded. The process is deemed complete once the third rotation transmitting assembly 260 reaches a hard stop or a force threshold as detected by the strain sensor 350. This indicates that the circular knife 444 has successfully dissected the tissue.

After the stapling and cutting sequences are complete, the user begins an unclamping sequence to release the anvil assembly 510 from the trocar member 274. The user may then remove the anvil assembly 510 and the reload 400, as well as the severed tissue from the resection site.

The adapter assembly 200 is then detached from the handle assembly 100. The shell housing 110 of the handle assembly 100 is opened and discarded, with the power handle 101 removed therefrom for reuse. The reload 400 is detached from the adapter assembly 200 and the electrical assembly 300 is detached from the adapter assembly 200 by detaching the strain sensor electrical connector 330 from the electrical connector 354 of the adapter assembly 200 and the pin connector assembly 320 from the drive coupling assembly 210 of the adapter assembly 200, as well as breaking any adhesive bond between the electrical assembly 300 and the adapter assembly 200. The reload 400 and the electrical assembly 300 is then discarded, and the adapter assembly 200 is cleaned and sterilized for reuse.

The separable electrical assembly 300 can allow low cost materials (e.g., flex cables, printed circuit boards, coatings, connectors, etc.) to be utilized as no cleaning is required and the usage time is short (e.g., single use). Accordingly, failures associated with cleaning and/or sterilization procedures, such as cracking or delamination of cables, breakdown of coatings, electronic component or connector failures, cracked internal traces, can be avoided.

Persons skilled in the art will understand that the structures specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. For example, the electrical assemblies of the present disclosure may be configured for use with a plurality of different reloads via a plurality of respective adapter assemblies that are each configured for actuation and manipulation by a powered handle assembly and/or a robotic surgical system. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A handheld electromechanical surgical device comprising:
   a handle assembly including a connecting portion having an electrical connector supported therein;
   an adapter assembly including an adapter housing and an outer tube extending distally from the adapter housing, the adapter housing selectively connectable to the connecting portion of the handle assembly;
   a reload including a reload housing selectively connectable to the outer tube of the adapter assembly, the reload including a circuit board assembly disposed within the reload housing; and
   an electrical assembly including a flex cable having an elongate body positionable against an outer surface of the adapter assembly, the flex cable including a proximal end and a distal end, the proximal end positionable within a cavity defined in the adapter housing and configured to electrically connect with the electrical connector of the handle assembly, and the distal end coupled to the circuit board assembly of the reload.

2. The surgical device according to claim 1, wherein the proximal end of the flex cable includes a pin connector assembly, the pin connector assembly configured to interface with the electrical connector of the handle assembly.

3. The surgical device according to claim 2, wherein the pin connector assembly includes electrical contact blades supported on a circuit board, the electrical contact blades configured to contact the electrical connector of the handle assembly when the adapter assembly is connected to the handle assembly.

4. The surgical device according to claim 1, wherein the distal end of the flex cable is permanently secured to the circuit board assembly of the reload.

5. The surgical device according to claim 1, wherein a distal portion of the flex cable extends through a port defined in the reload housing.

6. The surgical device according to claim 1, wherein the flex cable includes an adhesive disposed on a first side of the elongate body of the flex cable and positionable against the outer surface of the adapter assembly.

7. The surgical device according to claim 1, wherein the outer tube of the adapter assembly includes an electrical connector secured therein, the electrical connector electrically coupled to a strain sensor supported within the outer tube, and the flex cable includes a strain sensor electrical connector configured to mate with the electrical connector of the adapter assembly.

8. The surgical device according to claim 1, wherein the flex cable includes a printed circuit board disposed or integrated thereon.

9. The surgical device according to claim 8, wherein the printed circuit board is positioned along a proximal portion of the flex cable aligned with the adapter housing of the adapter assembly.

10. The surgical device according to claim 8, wherein wings extend laterally from the printed circuit board of the flex cable, the wings including an adhesive for securing the printed circuit board to the adapter assembly.

* * * * *